US008021403B2

(12) United States Patent
Wall et al.

(10) Patent No.: US 8,021,403 B2
(45) Date of Patent: Sep. 20, 2011

(54) SPINAL STAPLE SYSTEM

(75) Inventors: Eric J. Wall, Cincinnati, OH (US);
Donita I. Bylski-Austrow, Cincinnati, OH (US); Joseph E. Reynolds, Cincinnati, OH (US)

(73) Assignees: Children's Hospital Medical Center, Cincinnati, OH (US); SpineForm LLC, Cincinnati, OH (US)

( * ) Notice: Subject to any disclaimer, the term of this patent is extended or adjusted under 35 U.S.C. 154(b) by 1848 days.

(21) Appl. No.: 11/126,782

(22) Filed: May 11, 2005

(65) Prior Publication Data
US 2005/0277933 A1 Dec. 15, 2005

Related U.S. Application Data

(63) Continuation-in-part of application No. 10/862,660, filed on Jun. 7, 2004, now Pat. No. 7,481,830, which is a continuation of application No. 10/030,440, filed as application No. PCT/US00/18491 on Jul. 6, 2000, now Pat. No. 6,746,450.

(60) Provisional application No. 60/142,707, filed on Jul. 7, 1999.

(51) Int. Cl.
*A61B 17/80* (2006.01)

(52) U.S. Cl. ..................... 606/297; 606/246

(58) Field of Classification Search .......... 606/280–299, 606/300, 75, 70, 71, 322–328, 331; 411/457
See application file for complete search history.

(56) References Cited

U.S. PATENT DOCUMENTS

| 82,181 | A | * | 9/1868 | Tilestown | 402/14 |
|---|---|---|---|---|---|
| 431,175 | A | * | 7/1890 | Southwick | 24/36 |
| 758,881 | A | * | 5/1904 | Yost | 142/1 |
| 1,425,199 | A | * | 8/1922 | Hartley | 411/457 |
| 1,638,477 | A | * | 8/1927 | Dyer | 411/470 |
| 2,134,765 | A | * | 11/1938 | Putnam | 411/457 |
| 2,398,603 | A | * | 4/1946 | Soderberg | 411/457 |
| 2,919,621 | A | * | 1/1960 | Langdon | 411/481 |
| 3,693,616 | A | | 9/1972 | Roaf et al. | |
| 3,862,631 | A | | 1/1975 | Austin | |
| 4,041,939 | A | | 8/1977 | Hall | |
| 4,047,523 | A | | 9/1977 | Hall | |
| 4,047,524 | A | | 9/1977 | Hall | |
| 4,078,559 | A | | 3/1978 | Nissinen | |
| 4,401,112 | A | | 8/1983 | Rezaian | |
| 4,403,606 | A | | 9/1983 | Woo et al. | |

(Continued)

FOREIGN PATENT DOCUMENTS

DE 44 33 360 2/1996
(Continued)

OTHER PUBLICATIONS

Paper: "Endoscopic Nonfusion Spinal Hemiepiphysiodesis: Preliminary studies in a porcine model," by D. I. Bylski-Austrow et al., Jan. 1999.

(Continued)

*Primary Examiner* — Eduardo C Robert
*Assistant Examiner* — Mary Hoffman
(74) *Attorney, Agent, or Firm* — Baker & Daniels LLP

(57) ABSTRACT

A spinal correction system for the correction or arrest of scoliosis or spinal deformity in immature spines includes a bridge member, a pair of spaced apart legs extending substantially perpendicularly therefrom, and a fastener retaining portion extending substantially longitudinally from each end of the bridge member.

35 Claims, 15 Drawing Sheets

U.S. PATENT DOCUMENTS

| | | | |
|---|---|---|---|
| 4,434,796 A | 3/1984 | Karapetian et al. | |
| 4,454,875 A | 6/1984 | Pratt et al. | |
| 4,462,395 A | 7/1984 | Johnson | |
| 4,503,848 A | 3/1985 | Caspar et al. | |
| 4,570,618 A | 2/1986 | Wu | |
| 4,570,623 A | 2/1986 | Ellison et al. | |
| 4,573,454 A | 3/1986 | Hoffman | |
| 4,592,346 A | 6/1986 | Jurgutis | |
| 4,599,086 A | 7/1986 | Doty | |
| 4,651,724 A | 3/1987 | Berentey et al. | |
| 4,686,970 A | 8/1987 | Dove et al. | |
| 4,743,260 A | 5/1988 | Burton | |
| 4,776,851 A | 10/1988 | Bruchman et al. | |
| 4,793,335 A | 12/1988 | Frey et al. | |
| 4,841,960 A | 6/1989 | Garner | |
| 4,848,328 A | 7/1989 | Laboureau et al. | |
| 4,870,957 A | 10/1989 | Goble et al. | |
| 4,913,144 A | 4/1990 | Del Medico | |
| 4,943,292 A | 7/1990 | Foux | |
| 4,955,910 A | 9/1990 | Bolesky | |
| 4,960,420 A | 10/1990 | Goble et al. | |
| 4,966,600 A | 10/1990 | Songer et al. | |
| 4,998,936 A | 3/1991 | Mehdian | |
| 5,002,574 A | 3/1991 | May et al. | |
| 5,011,484 A | 4/1991 | Breard | |
| 5,030,220 A | 7/1991 | Howland | |
| D320,081 S | 9/1991 | Johnson | |
| 5,053,038 A | 10/1991 | Sheehan | |
| 5,092,866 A | 3/1992 | Breard et al. | |
| 5,092,868 A | 3/1992 | Mehdian | |
| 5,108,395 A | 4/1992 | Laurain | |
| 5,116,340 A | 5/1992 | Songer et al. | |
| 5,147,361 A | 9/1992 | Ojima et al. | |
| 5,180,393 A | 1/1993 | Commarmond | |
| 5,199,146 A | 4/1993 | Grover et al. | |
| D340,284 S | 10/1993 | Johnson | |
| 5,261,910 A | 11/1993 | Warden et al. | |
| 5,306,301 A | 4/1994 | Graf et al. | |
| 5,318,566 A | 6/1994 | Miller | |
| 5,324,290 A | 6/1994 | Zdeblick et al. | |
| 5,352,229 A | 10/1994 | Goble et al. | |
| 5,387,213 A | 2/1995 | Breard et al. | |
| 5,395,372 A | 3/1995 | Holt et al. | |
| 5,395,374 A | 3/1995 | Miller et al. | |
| 5,405,391 A | 4/1995 | Hednerson et al. | |
| 5,415,658 A | 5/1995 | Kilpela et al. | |
| 5,415,661 A | 5/1995 | Holmes | |
| 5,417,690 A | 5/1995 | Sennett et al. | |
| 5,423,820 A | 6/1995 | Miller et al. | |
| 5,425,767 A | 6/1995 | Steininger et al. | |
| 5,449,359 A | 9/1995 | Groiso | |
| 5,456,722 A | 10/1995 | McLeod et al. | |
| D364,462 S | 11/1995 | Michelson | |
| 5,476,465 A | 12/1995 | Preissman | |
| 5,496,318 A | 3/1996 | Howland et al. | |
| 5,502,942 A * | 4/1996 | Gras et al. | 52/511 |
| 5,536,270 A | 7/1996 | Songer et al. | |
| 5,540,698 A | 7/1996 | Preissman | |
| 5,540,703 A | 7/1996 | Barker, Jr. et al. | |
| 5,545,168 A | 8/1996 | Burke | |
| 5,569,253 A | 10/1996 | Farris et al. | |
| 5,603,713 A | 2/1997 | Aust et al. | |
| 5,603,714 A | 2/1997 | Kaneda et al. | |
| D378,409 S * | 3/1997 | Michelson | D24/145 |
| 5,607,425 A | 3/1997 | Rogozinski | |
| 5,609,634 A | 3/1997 | Voydeville | |
| 5,620,443 A | 4/1997 | Gertzbein et al. | |
| 5,649,927 A | 7/1997 | Kilpela et al. | |
| 5,653,711 A | 8/1997 | Hayano et al. | |
| 5,662,655 A | 9/1997 | Laboureau et al. | |
| 5,669,917 A | 9/1997 | Sauer et al. | |
| 5,693,046 A | 12/1997 | Songer et al. | |
| 5,702,395 A | 12/1997 | Hopf | |
| 5,702,399 A | 12/1997 | Kilpela et al. | |
| 5,707,395 A | 1/1998 | Li | |
| 5,713,900 A | 2/1998 | Benzel et al. | |
| 5,720,747 A | 2/1998 | Burke | |
| 5,725,582 A | 3/1998 | Bevan et al. | |
| 5,741,260 A | 4/1998 | Songer et al. | |
| 5,908,421 A | 6/1999 | Beger | |
| 6,017,345 A | 1/2000 | Richelsoph | |
| 6,066,140 A | 5/2000 | Gertzbein et al. | |
| 6,228,085 B1 | 5/2001 | Theken et al. | |
| 6,231,610 B1 | 5/2001 | Geisler | |
| 6,235,059 B1 | 5/2001 | Benezech et al. | |
| 6,296,643 B1 | 10/2001 | Hopf et al. | |
| 6,299,613 B1 | 10/2001 | Ogilvie et al. | |
| 6,309,393 B1 | 10/2001 | Tepic et al. | |
| 6,325,805 B1 | 12/2001 | Ogilvie et al. | |
| 6,336,928 B1 | 1/2002 | Guerin et al. | |
| 6,436,099 B1 | 8/2002 | Drewry et al. | |
| 6,517,564 B1 | 2/2003 | Grafton et al. | |
| 6,551,320 B2 | 4/2003 | Lieberman | |
| 6,616,669 B2 | 9/2003 | Ogilvie et al. | |
| 6,623,484 B2 | 9/2003 | Betz et al. | |
| 6,746,450 B1 | 6/2004 | Wall et al. | |
| 2004/0220569 A1 | 11/2004 | Wall et al. | |

FOREIGN PATENT DOCUMENTS

| | | |
|---|---|---|
| EP | 0 026 970 A1 | 4/1981 |
| EP | 0 478 470 A1 | 1/1992 |
| EP | 0 545 830 A1 | 6/1993 |
| EP | 0 552 109 A | 7/1993 |
| EP | 0 625 336 A2 | 11/1994 |
| FR | 2 709 410 | 3/1995 |
| JP | 63-95060 | 4/1988 |
| JP | 3-75717 U | 7/1991 |
| JP | 7-79998 | 3/1995 |
| JP | 7-163580 | 6/1995 |
| JP | 8-507458 | 8/1996 |
| JP | 8-229052 | 9/1996 |
| JP | 10-277070 | 10/1998 |
| JP | 11-056870 | 2/1999 |
| WO | WO 91/16018 | 10/1991 |
| WO | WO 94/01057 | 1/1994 |
| WO | WO 94/26192 | 11/1994 |
| WO | WO 98/17189 | 4/1998 |
| WO | WO 98/48718 | 11/1998 |
| WO | WO 98/51226 | 11/1998 |

OTHER PUBLICATIONS

"A Mature Look at Epiphyseal Stapling," Water P. Blount, MD, Clinical Orthopaedics and Related Research, No. 77, Jun. 1971, pp. 158-163.

"An Analysis of the Effect of the Zielke Operation on S-shaped Curves in Idiopathic Scoliosis: A Follow-up Study Revealing Some Skeletal and Soft Tissue Factors Involved in Curve Progression," by A.S. Wojcik, MD et al., Spine, vol. 15, No. 8, 1990.

"An Operation for Stapling Vertebral Bodies in Congenital Scoliosis," by A.D. Smith et al., The Journal of Bone and Joint Surgery, vol. 36-A, No. 2, pp. 342-348, Apr. 1954.

"Attempted Treatment of Scoliosis by Unilateral Vertebral Epiphyseal Arrest," by H.R. McCarroll, MD et al., The Journal of Bone and Joint Surgery, vol. 42-A, No. 6, Sep. 1960.

"CDH: preliminary report on a new anterior spinal instrumentation," by C. Hopf et al., European Spine Journal, Spring 1994.

"Comparison Between Single-Screw and Triangulated, Double-Screw Fixation in Anterior Spine Surgery: A Biomechanical Test," by Michael Ogon, MD et al., Spine, vol. 21, No. 23, 1996.

"Control of Bone Growth by Epiphyseal Stapling: A Preliminary Report," by Walter P. Blount, MD et al., The Journal of Bone and Joint Surgery, vol. 31-A, No. 3, Jul. 1949.

"Convex Anterior and Posterior Hemiarthrodesis and Hemiepiphysiodesis in Young Children with Progressive Congenital Scoliosis ," by Robert B. Winter, Journal of Pediatric Orthopaedics, vol. 1, No. 4, 1981.

"Convex Growth Arrest for Progressive Congenital Scoliosis Due to Hemivertebrae," Robert B. Winter, MD et al., Journal of Pediatric Orthopaedics, vol. 8, No. 6, 1988.

"Endoscopic Discectomy Increases Thoracic Spine Flexibility as Effectively as Open Discectomy: A Mechanical Study in a Porcine Model," by Eric J. Wall, et al., Spine vol. 23(1), pp. 9-15, Jan. 1, 1998.

"Growth Arrest for Progressive Scoliosis: Combined Anterior and Posterior Fusion of the Convexity," by Terry Andrew et al., The Journal of Bone and Joint Surgery, vol. 67-B, No. 2, Mar. 1985.

"Growth Modification in the Treatment of Scoliosis," by Harry Piggot, FRCS, Orthopedics, vol. 10, No. 6, Jun. 1987.

"Histologic Arrangements from Biopsies of Epiphyseal Plates of Children Before and After Stapling," by Charles Weer Goff, MD, American Journal of Orthopedics, May 1967.

"Influence of Epiphyses on the Regulation of Bone Growth," E.C.B. Hall-Craggs, Nature, vol. 221, Mar. 29, 1969.

"Mechanical Modulation of Vertebral Body Growth; Implications for Scoliosis Progression," by Ian A.F. Stokes, Ph.D. et al., Spine, vol. 21, No. 10, 1996.

"Operative Treatment of Scoliosis With Cotrel-Dubousset-Hopf Instrumentation: New Anterior Spinal Device," by Christof G. Hopf et al., Spine, vol. 22, No. 6, 1997.

"Progression of Vertebral Wedging in an Asymmetrically Loaded Rat Tail Model," by Peter L. Mente, Ph.D. et al., Spine, vol. 22, No. 12, 1997.

"Retardation of Bone Growth by a Wire Loop," by S.L. Haas, MD, The Journal of Bone and Joint Surgery, vol. 27, No. 1, Jan. 1945.

"The Cure of Experimental Scoliosis by Directed Growth Control," by I. William Nachlas, MD et al., The Journal of Bone and Joint Surgery, vol. 33-A, No. 1, 1951.

"The Effect of Epiphysial Stapling on Growth in Length of the Rabbit's Tibia and Femur," by E.C.B. Hall-Craggs et al., The Journal of Bone and Joint Surgery, vol. 51B, No. 2, May 1969.

"The Effects of Mechanical Forces on Bones and Joints: Experimental Study on the Rat Tail," by Ugo E. Pazzaglia et al., The Journal of Bone and Joint Surgery, vol. 79-B, No. 6, Nov. 1997.

"The Prediction of Curve Progression in Untreated Idiopathic Scoliosis During Growth," by John E. Lonstein et al., The Journal of Bone and Joint Surgery, vol. 66-A, No. 7, Sep. 1984.

"The Treatment of Progressive Scoliosis by Unilateral Growth-Arrest," by Robert Roaf, The Journal of Bone and Joint Surgery, vol. 45-B, No. 4, Nov. 1963.

"Transpedicular Convex Anterior Hemiepiphysiodesis and Posterior Arthrodesis for Progressive Congenital Scoliosis," by Andrew G. King, MB, et al., Spine, vol. 17, No. 8S, 1992.

"Vertebral Growth and Its Mechanical Control," by Robert Roaf, The Journal of Bone and Joint Surgery, vol. 42-B, No. 1, Feb. 1960.

"Growth Plate Forces in the Adolescent Human Knee: A Radiographic and Mechanical Study of Epiphyseal Staples," by Donita I. Bylski-Austrow et al., Journal of Pediatric Orthopaedics, Nov./Dec. 2001 21:817-823.

"An Innovative Technique of Vertebral Body Stapling for the Treatment of Patients With Adolescent Idiopathic Scoliosis: A Feasibility, Safety, and Utility Study," by Randal R. Betz MD et al., Spine, vol. 28, No. 20S, pp. S255-S265, 2003.

* cited by examiner

SPINAL STAPLE SYSTEM

CROSS-REFERENCE TO RELATED APPLICATIONS

This application is a continuation-in-part of U.S. patent application Ser. No. 10/862,660, filed Jun. 7, 2004, now U.S. Pat. No. 7,481,830 which is a continuation of U.S. patent application Ser. No. 10/030,440, filed Jan. 7, 2002, now U.S. Pat. No. 6,746,450, which is the national phase under 35 U.S.C. §371 of PCT International Application No. PCT/US00/18491, having a filing date of Jul. 6, 2000, which claims the benefit of U.S. Provisional Patent Application Ser. No. 60/142,707, filed Jul. 7, 1999, all of which are expressly incorporated by reference herein.

BACKGROUND OF THE INVENTION

This invention relates to devices for use in the correction, arresting or slowing of abnormal curvature of the spine, including scoliosis, hyperlordosis and hypokyphosis.

Juvenile and adolescent scoliosis is a disorder of the growing spine in which a predominantly lateral curvature develops. Curves over 40° can require surgical correction due to the high risk of future progression during adulthood. One typical procedure, often called "posterior approach scoliosis surgery," is one of the most invasive human surgeries in orthopedics. During a typical three to eight hour procedure, a surgeon strips the strong posterior muscles off of the spine for bone exposure, then attaches two metal rods to the spine with hooks, wires, or screws. An alternative scoliosis approach is through the anterior chest via thoracotomy or thoracoscopy. After multi-level discectomy and fusion, large screws are placed across the vertebral bodies, and then the screws and vertebrae are compressed together by means of a vertical rod.

Staples are often used in orthopaedics to fix two bones or pieces of bone together, such as would be required for osteotomy (bone cutting), or fracture stabilization. Staples typically used for these purposes are disclosed in U.S. Pat. Nos. 4,434,796 by Karapetian; 3,862,621 to Austin; 4,841,960 to Garner; 4,848,328 to Laboureau et al.; 5,449,359 to Groiso; 5,053,038 to Sheehan; and 4,913,144 to Del Medico.

Orthopaedic staples are also used in the fixation of soft tissue to bone, such as tendon or shoulder tissue. Staples typically used for these purposes are described in U.S. Pat. Nos. 5,352,229 to Goble et al.; 4,462,395 to Johnson; 4,570,623 to Ellison et al.; 4,454,875 to Pratt et al.; D320,081 to Johnson; and D340,284 to Johnson.

In addition, several screws with a linkage plate or rod have been developed for anterior spine fixation and are described in U.S. Pat. Nos. 5,324,290 to Zdeblick et al.; and 4,041,939 to Hall.

Additional U.S. Patents disclose spine staples, for example U.S. Pat. Nos. 4,047,523 to Hall; 4,047,524 to Hall; 5,395,372 to Holt et al.; D378,409 to Michelson; and D364,462 to Michelson.

The inventors have developed a novel procedure and spinal correction system for correcting scoliosis in children that takes advantage of future spine growth to correct the scoliosis. This procedure relies upon slowing spine epiphyseal growth on the convex side of the scoliosis curve with a novel hemiepiphyseal spinal correction system.

The novel procedure using the novel spinal correction system requires only about one-fourth of the time necessary for conventional implantation techniques and may be performed using minimally invasive endoscopic procedures. In addition, the novel spinal correction system has an extremely low profile which reduces the risk of neurological complications.

This new procedure illustratively uses a novel system of staples and screws to provide anterior non-fusion (no bone graft) correction of scoliosis in children with significant growth remaining. The procedure can be performed entirely endoscopically in as little as one hour of surgical time. This procedure using the novel spinal staple avoids the complex rod-screw linkage of current anterior scoliosis corrective systems. It also holds the potential for making correction an outpatient procedure and minimizes blood loss during surgery.

Existing spinal implants do not effectively take advantage of the hemiepiphysiodesis principle of altering spine growth and allowing for gradual correction through asymmetric growth. Prior art bone staples used to fix two bones or pieces of bone together, for example, are not designed to perform hemiepiphysiodesis, and are not designed or able to resist the forces of spinal motion and growth without significant splay. Orthopaedic staples used to fix soft tissue to bone are not designed to span two bones or two pieces of bone. Thus, such staples are inapplicable to the novel procedure for the correction of scoliosis in children.

The other staples mentioned above were not designed for spine hemiepiphysiodesis and are instead intended for other purposes. For example, U.S. Pat. No. 4,041,939 to Hall discloses small staples to stabilize a screw-bone interface and to prevent migration or plowing of a screw through a bone. Likewise, U.S. Pat. No. 4,047,524 to Hall discloses a spinal staple meant to stabilize the screw-bone interface of a screw and rod system. U.S. Pat. No. 4,047,523 to Hall discloses a surgical sacral anchor implant that is half of a staple blade affixed to a cable for the fixation of the lower end of the spine. U.S. Pat. No. 5,395,372 to Holt et al., is a spinal staple that holds a strut bone graft in place and is designed for use after vertebrectomy.

Thus, there exists a need for an effective spinal correction system that is small and designed to span vertebral endplate growth centers on either side of a disk.

Devices such as screws or staples for the treatment of skeletal deformity have been know to disrupt, or cut through, bone during normal use. More particularly, epiphyseal devices for the arrest or correction of spinal deformity may disrupt the surrounding bone due to high loads carried by the fastening mechanism, such as a staple leg. This disruption, often called "bone plowing," occurs under physiological loads due to growth and to joint motion. Bone plowing can reduce the force magnitudes applied to the bone's growth plates and may also be associated with device deformation or dislodgment.

As a staple plows through bone it may partially dislodge such that the staple crown moves away from the bone. As the staple crown moves away from the bone, a greater moment is placed about the staple leg, which can cause the staple to deflect or plastically bend and splay open the legs. In severe cases, the staple may dislodge, resulting in other potential complications.

As such, there exists a need for an effective spinal correction system that reduces the likelihood of bone plowing by spreading the load over a large area of vertebral bone.

SUMMARY OF THE INVENTION

A spinal correction system according to an illustrative embodiment of the present invention includes a spinal staple having a bridge member with a length sufficient to span the vertebral endplate growth centers on either side of a vertebral disk. A pair of spaced apart wedged-shaped legs extend downwardly from the end of the bridge member and are of such a length as to penetrate no more than about half way into the depth of a vertebra. Fastener retaining portions extend horizontally outward from the opposite ends of the bridge member and define passageways therethrough adapted to receive fasteners such as screws and the like. The fastener retaining portions are proportioned so that when two or more of the spinal staples of the invention are arranged in end-to-end adjoining relationship, the fastener retaining portions extending from the abutting ends lie side by side.

The legs of the staple are equipped with barbs to resist backing out or loosening of the staple after it has been affixed to a vertebra. In addition, the fastener retaining portions have barbs or projections extending from a lower surface thereof to promote fixation of the staple in a vertebra. Optionally, the staple may be provided with a threaded cannulated post extending upward from the upper surface of the bridge member to allow attachment of a threaded removable, cannulated impaction device. Further, additional surgical hardware may be conveniently affixed to the staple by means of the threaded post. The staple may also include anti-rotation members extending outwardly from the legs and configured to assist in the prevention of rotational deformity.

The legs of the staple have a transverse cross-sectional area (defined by width and length of the legs) configured to ensure adequate contact surface against the vertebra to compress sufficient endplate growth areas, to provide an appropriate pattern of compression distribution, to prevent plowing, and to reduce joint motion. Illustratively, the transverse cross-sectional area of the legs is at least 10 percent of the cross-sectional area of the respective vertebra, and the length of the legs is up to 40 percent of the transverse width of the respective vertebra. The ratio of the leg width to its length is illustratively greater than about one-half to accommodate variations in patient mass and size, and the cross-sectional area of the vertebrae as a function of age and vertebral level.

The invention will be further described and illustrated in conjunction with the following detailed description and appended drawings.

DETAILED DESCRIPTION OF THE DRAWINGS

Figure 1:
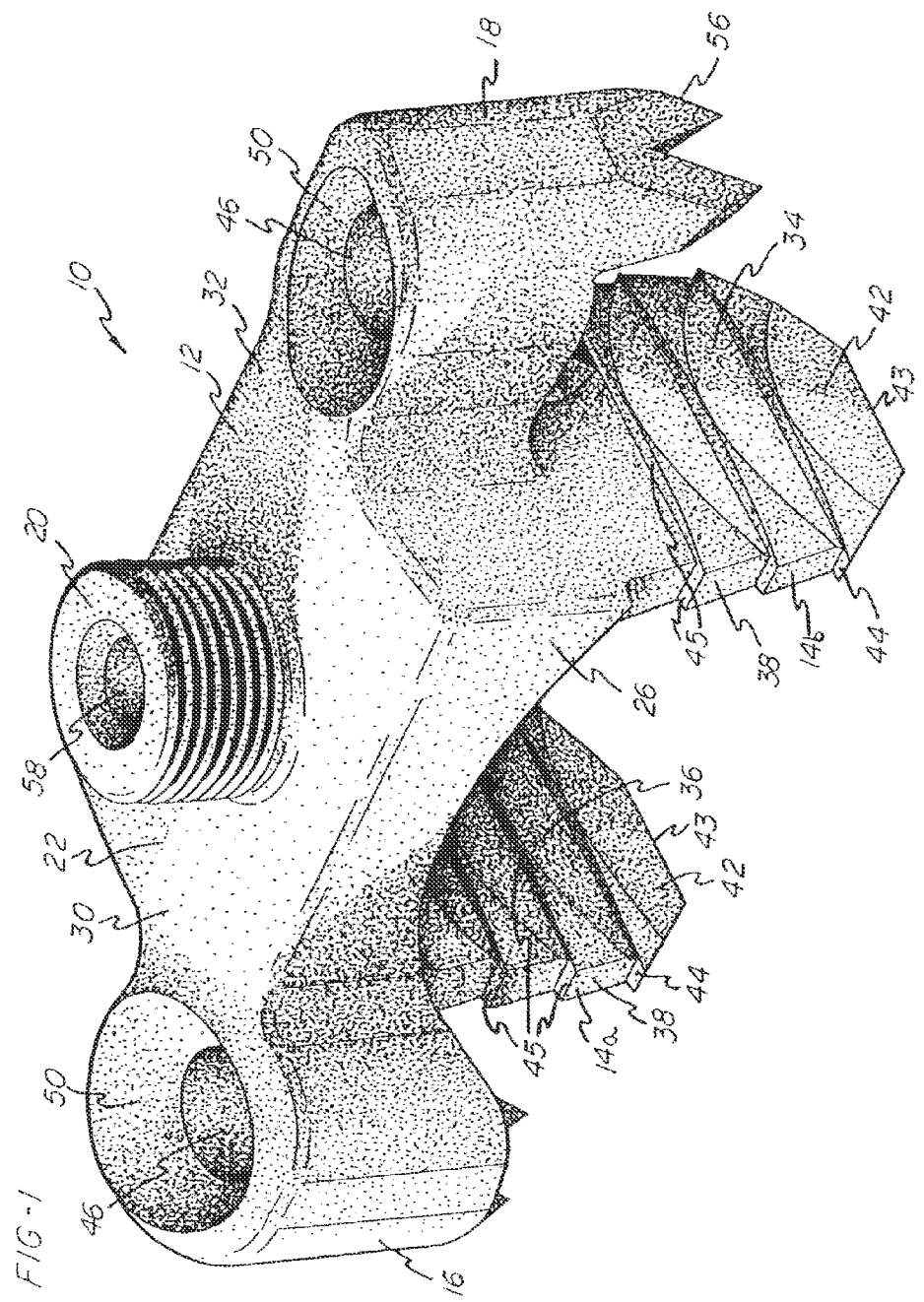
FIG. 1 is a perspective view of a spinal staple in accordance with the invention.

Referring to FIGS. 1-6, a spinal staple 10 constructed in accordance with an illustrative embodiment of the invention is shown. The staple 10 includes a bridge member 12, a pair of spaced apart legs 14, a left fastener retaining portion 16, a right fastener retaining portion 18, and an attachment member, illustratively a threaded post 20. Although reference will be made throughout this description to terms implying direction such as left, right, front, back, upper and lower, these terms are used only for convenience in describing the staple 10 and should not be read as limiting the staple 10 to any particular orientation.

The bridge member 12 includes an upper surface or crown 22, an opposed lower surface 24, a front side 26, an opposed back side 28, a left end 30 and an opposed right end 32. The upper surface 22 is substantially planar in a direction extending from the left end 30 to the right end 32, and is convex in a direction from the front side 26 to the back side 28, as may best be seen in FIG. 5 when the staple 10 is viewed from one of the ends. The lower surface 24 is concave in a direction from the left end 30 to the right end 32 and from the front side 26 to the back side 28, as may best be seen in FIGS. 2 and 3. The bridge member 12 thus defines a pair of cooperating arches, a first arch extending between the left and right ends 30 and 32 and a second arch extending between the front and back sides 26 and 28.

Figure 2:
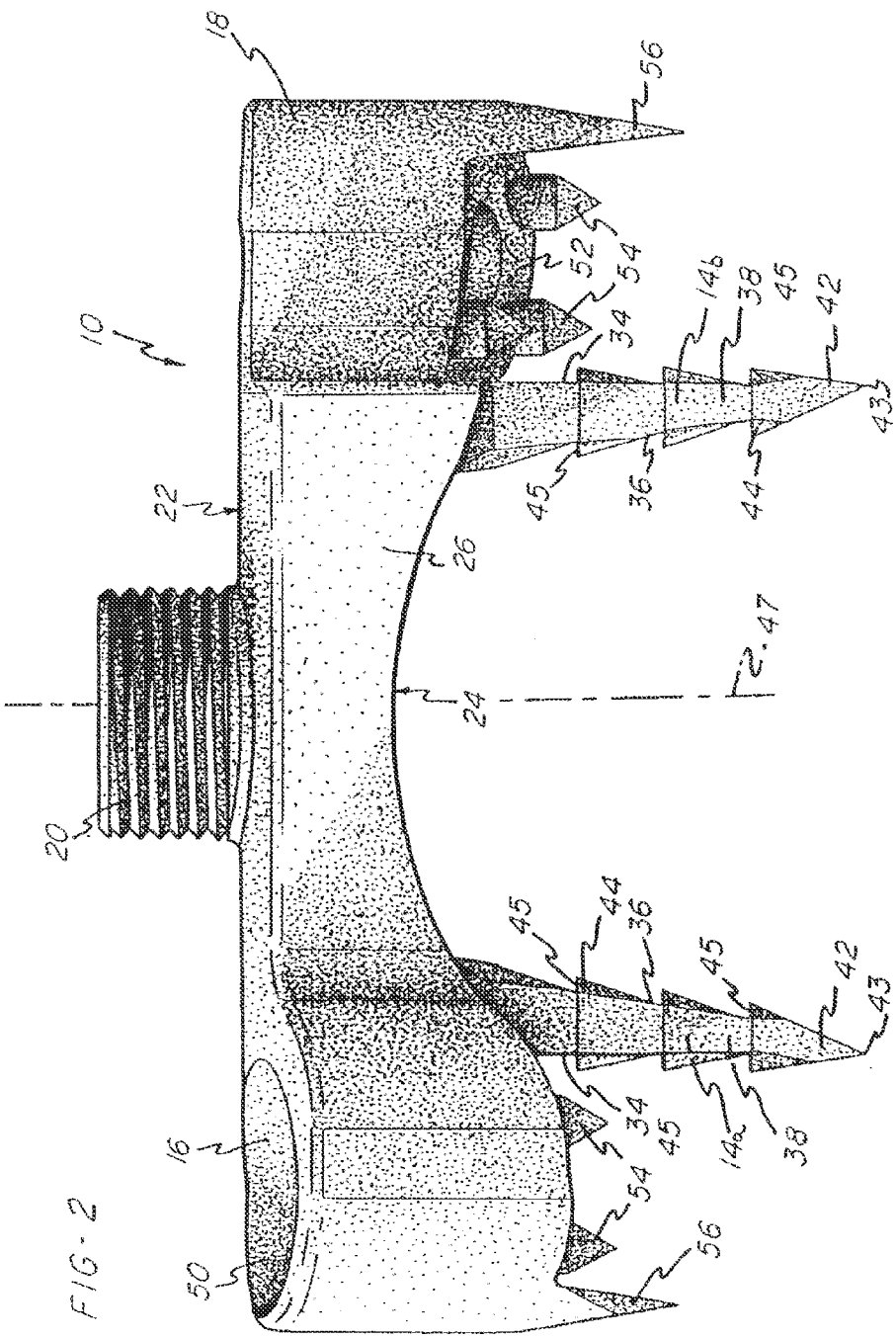
FIG. 2 is a front elevation view of the spinal staple of FIG. 1.
Figure 3:
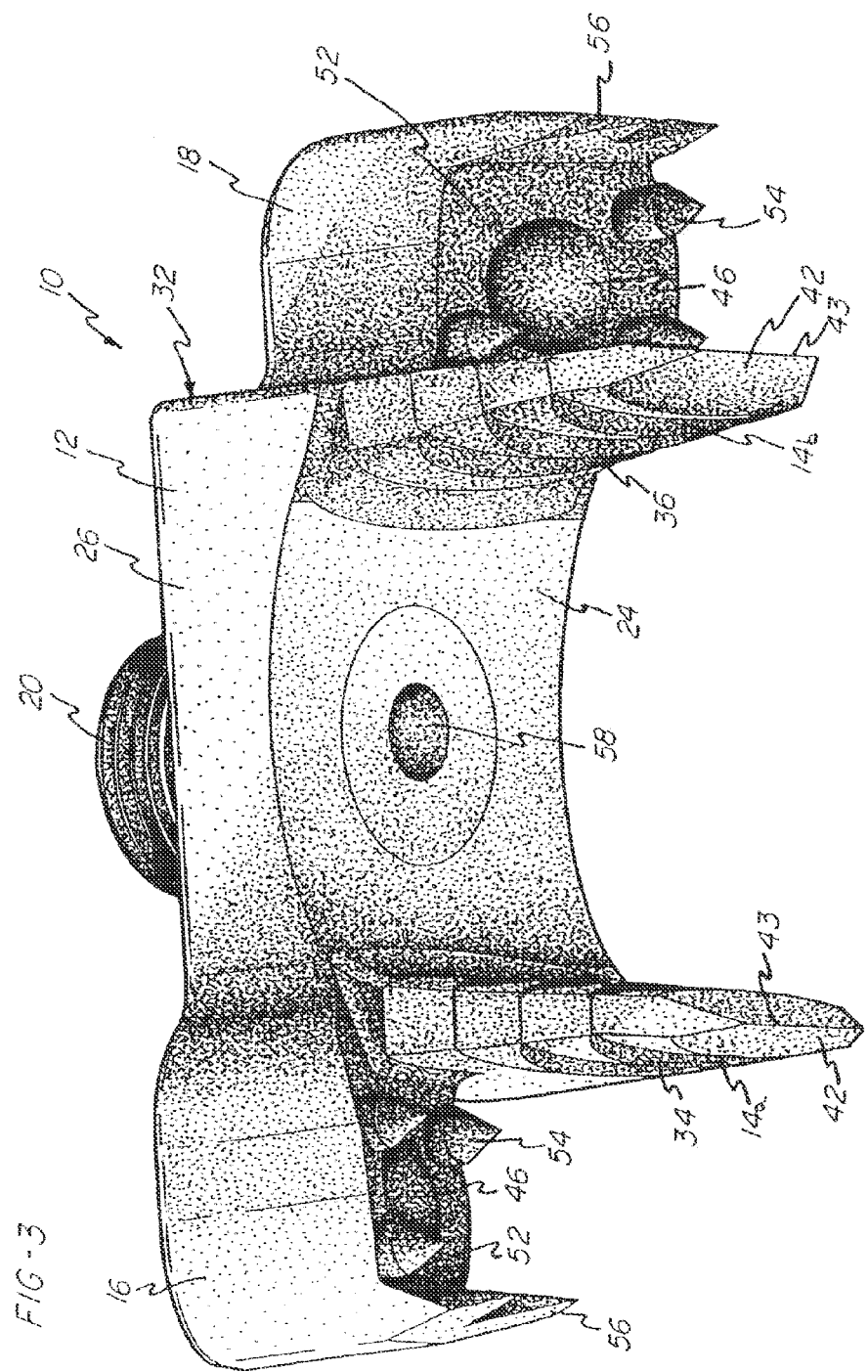
FIG. 3 is a perspective view of the spinal staple showing the underside of the staple.

Left and right legs 14a and 14b extend downwardly from the lower surface 24 at the left and right ends 30 and 32, and are substantially wedge-shaped. Each leg 14 has an outer surface 34, an opposed inner surface 36 such that the inner surfaces 36 are facing each other, a front surface 38, and an opposed back surface 40. Each of the legs 14 has a width as measured from the front surface 38 to the back surface 40, which is substantially equal to the width of the bridge member 12 as measured from the front side 26 to the back side 28. As shown in FIGS. 1-3, the width of each leg 14 is several times greater than the thickness of the respective leg 14, as measured from the outer surface 34 to the inner surface 36. The legs 14 narrow slightly from the front surface 38 to the back surface 40 toward their respective tips 42 which are sharply tapered to define a blade edge 43. Barbs 44 illustratively project outwardly from each of the outer, inner, front, and back surfaces 34, 36, 38 and 40, respectively.

Each barb 44 includes a retaining surface 45 facing generally away from the respective tip 42 and facing generally toward the bridge member 12. As such, the barbs 44 are adapted to inhibit withdrawal movement of the staple 10 once the staple 10 has been positioned in its fixation environment, such as a vertebra. The inner surface 36 of the legs 14 are preferably splayed, or angled, away from each other at an angle of about 10° to 20° as measured from a vertical plane 47 extending perpendicularly through the cross-section of the bridge member 12. The outer surfaces 34 of the legs 14 extend downwardly substantially perpendicular to the bridge member 12 and substantially parallel to the vertical plane 47.

Figure 6:
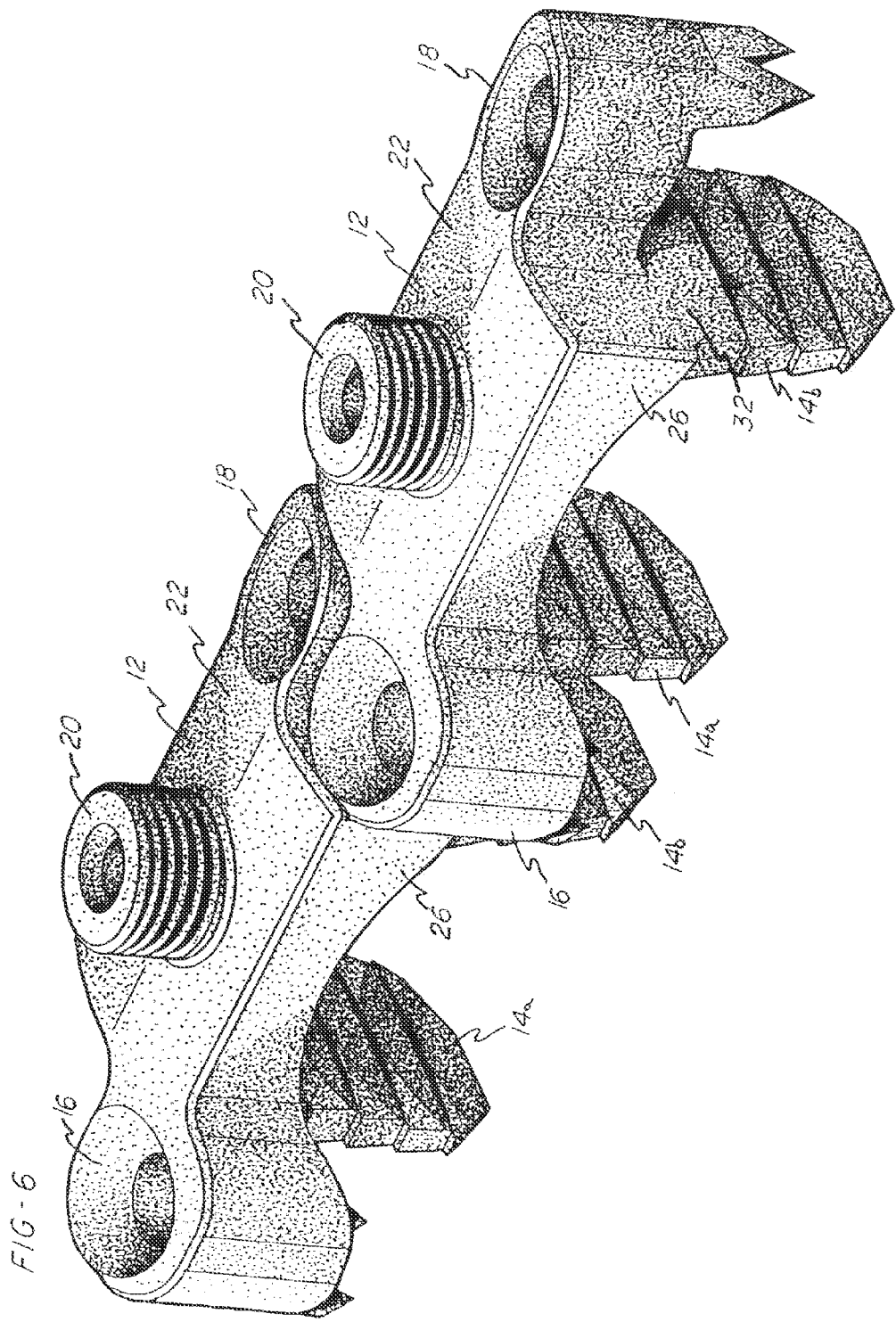
FIG. 6 is a perspective view of two of the spinal staples in accordance with the invention aligned in end-to-end adjoining relationship.
Figure 8:
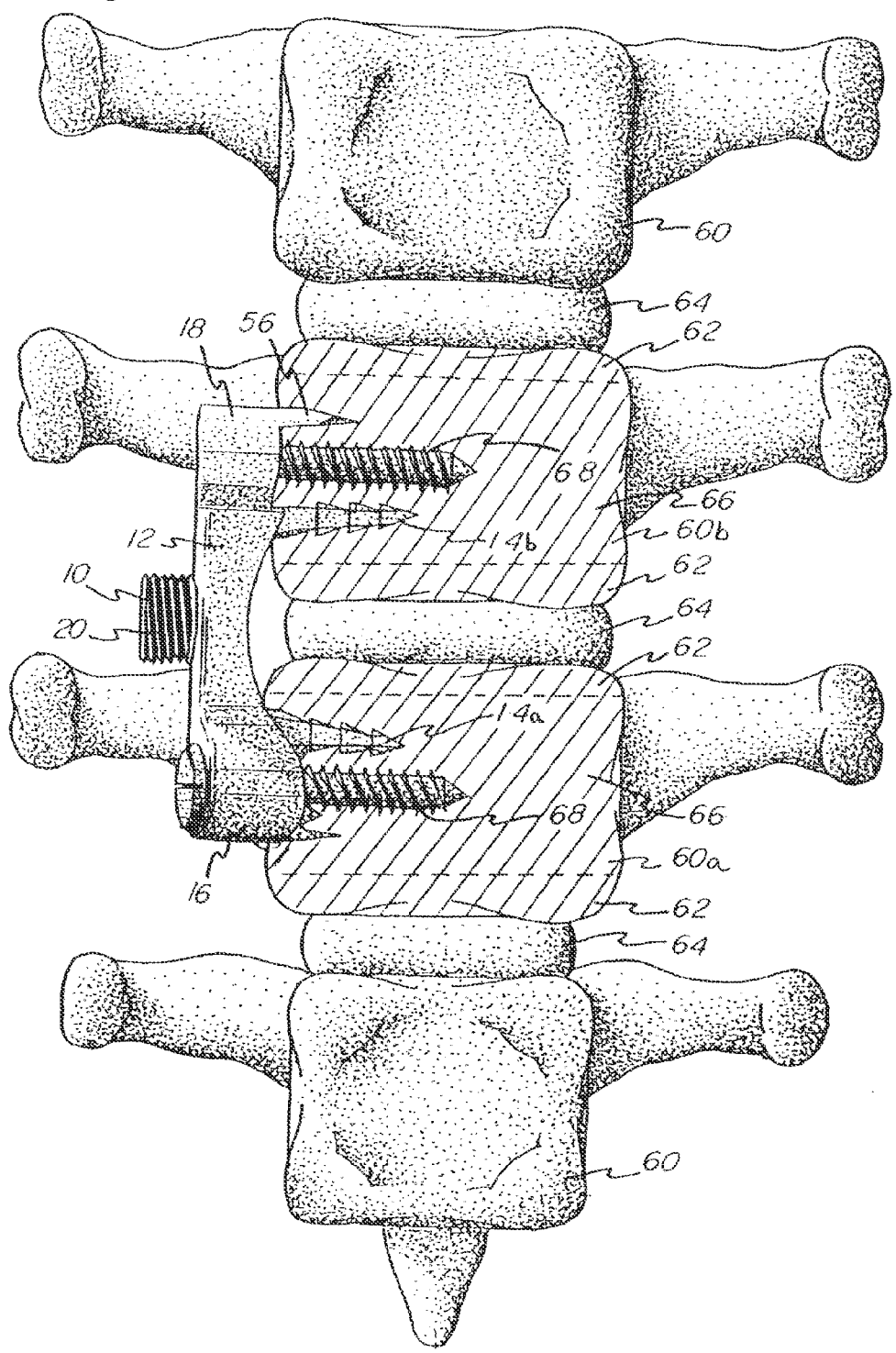
FIG. 8 is an elevation view in partial section of a spinal correction system in accordance with the invention affixed to two vertebrae so as to span two endplate growth centers and an intervening disk.

The left fastener retaining portion 16 extends outwardly from the bridge member left end 30. The right fastener retaining portion 18 extends outwardly from the bridge member right end 32. Each of the fastener retaining portions 16, 18 define a passageway 46 therethrough adapted to receive therein a fastener 68, such as a screw (FIG. 8). The fastener retaining portions 16, 18 and the passageways 46 are adapted to guide a fastener 68 in a direction substantially parallel to the legs 14. Also, the fastener retaining portions 16, 18 each include front and back sides 49 and 51 and are proportioned so that when two of the staples 10 are in end-to-end abutting relation, as shown in FIG. 6, then the fastener retaining portions 16, 18 extending from abutting ends are in side-to-side adjoining relation to each other. In other words, the left fastener retaining portion 16 on one staple 10 lies alongside the right fastener retaining portion 18 of the other staple 10. Moreover, the back side 51 of the left fastener retaining portion 16 of a first staple 10 is positioned in proximity to and facing the front side 49 of the right fastener retaining portion 18 of an adjacent second staple 10.

Figure 4:
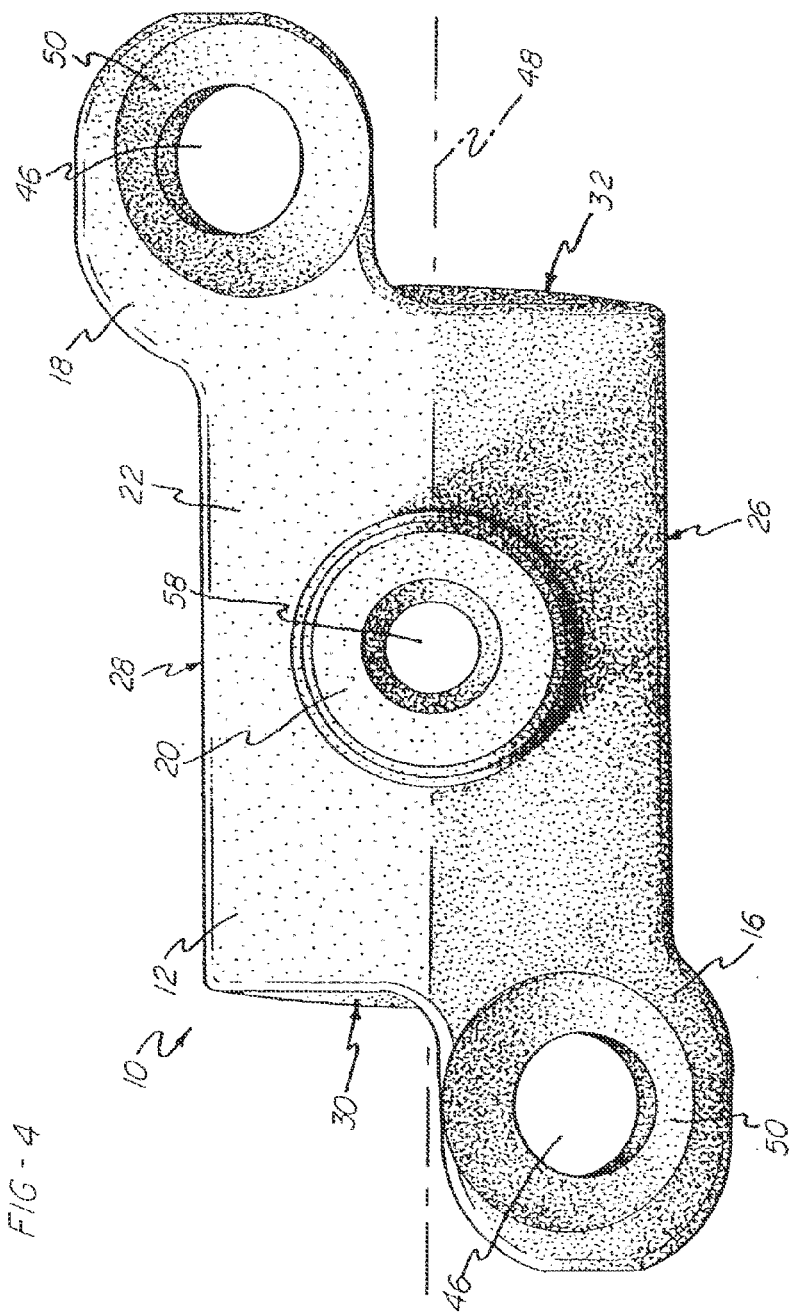
FIG. 4 is a top plan view of the spinal staple.
Figure 5:
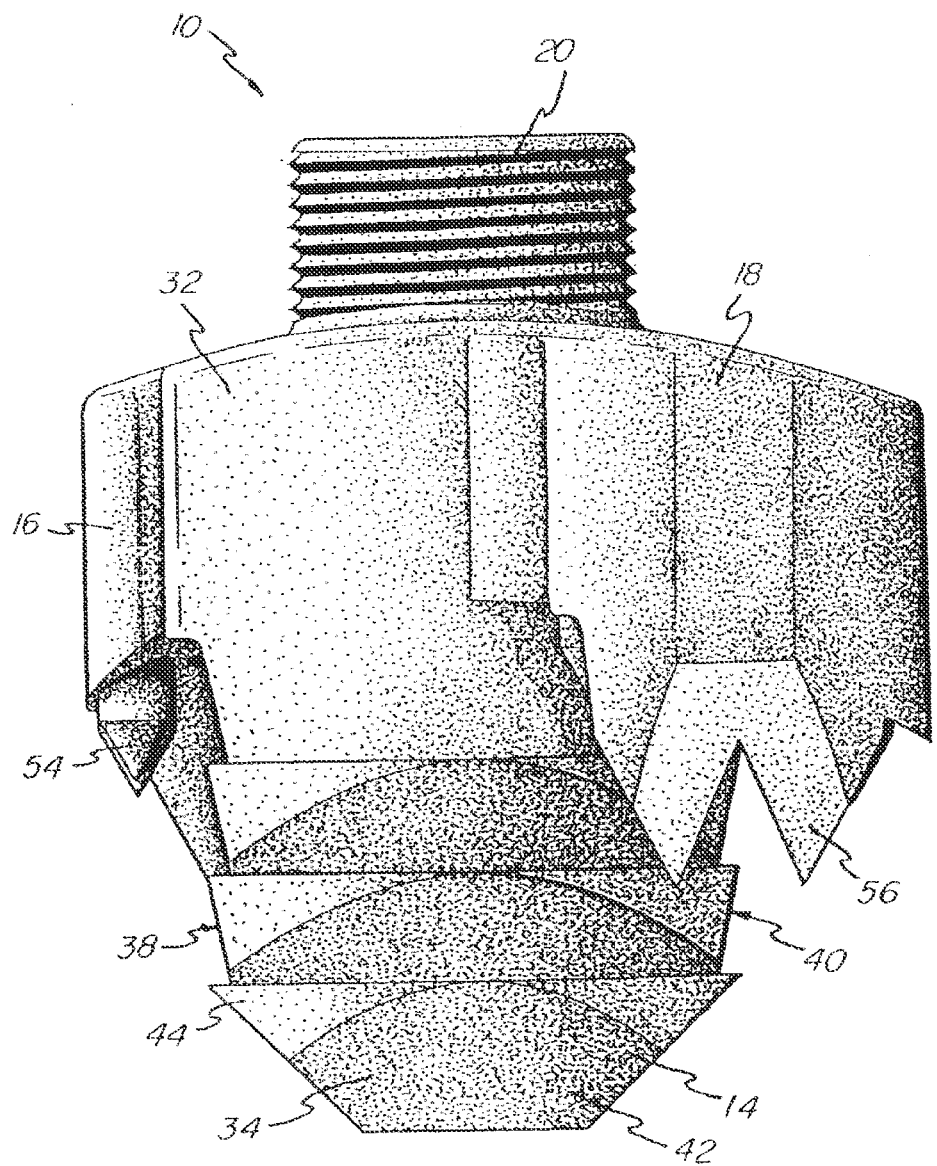
FIG. 5 is an end elevation view of the spinal staple.

As may be seen in FIG. 4, a longitudinal axis 48 extends through the center of the staple 10 from the left end 30 to the right end 32. In an illustrative embodiment, the left and right fastener retaining portions 16, 18 lie on opposite sides of the longitudinal axis 48.

Figure 9:
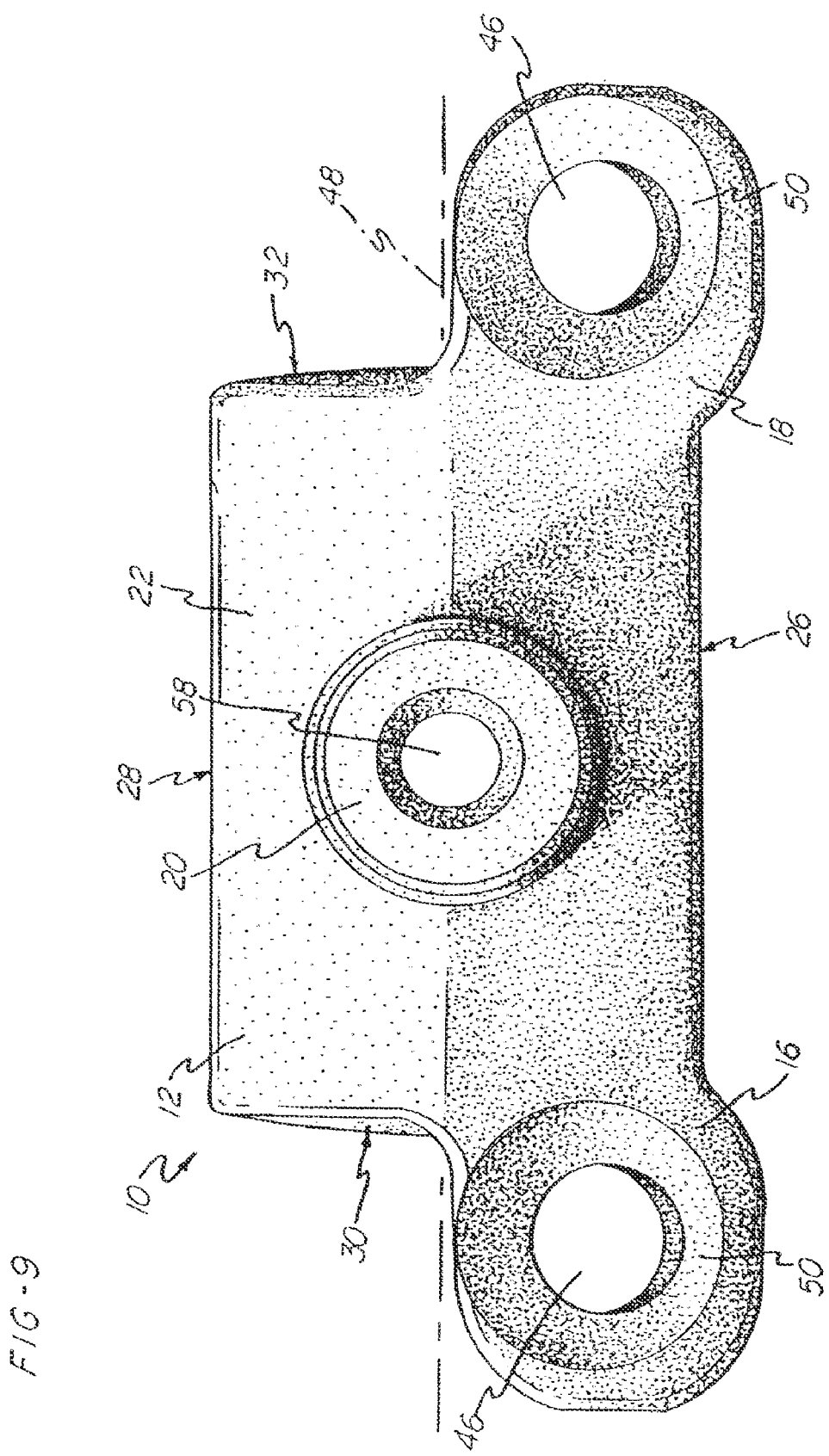
FIG. 9 is a top plan view of an alternative embodiment of the spinal staple in accordance with the invention.
Figure 10:
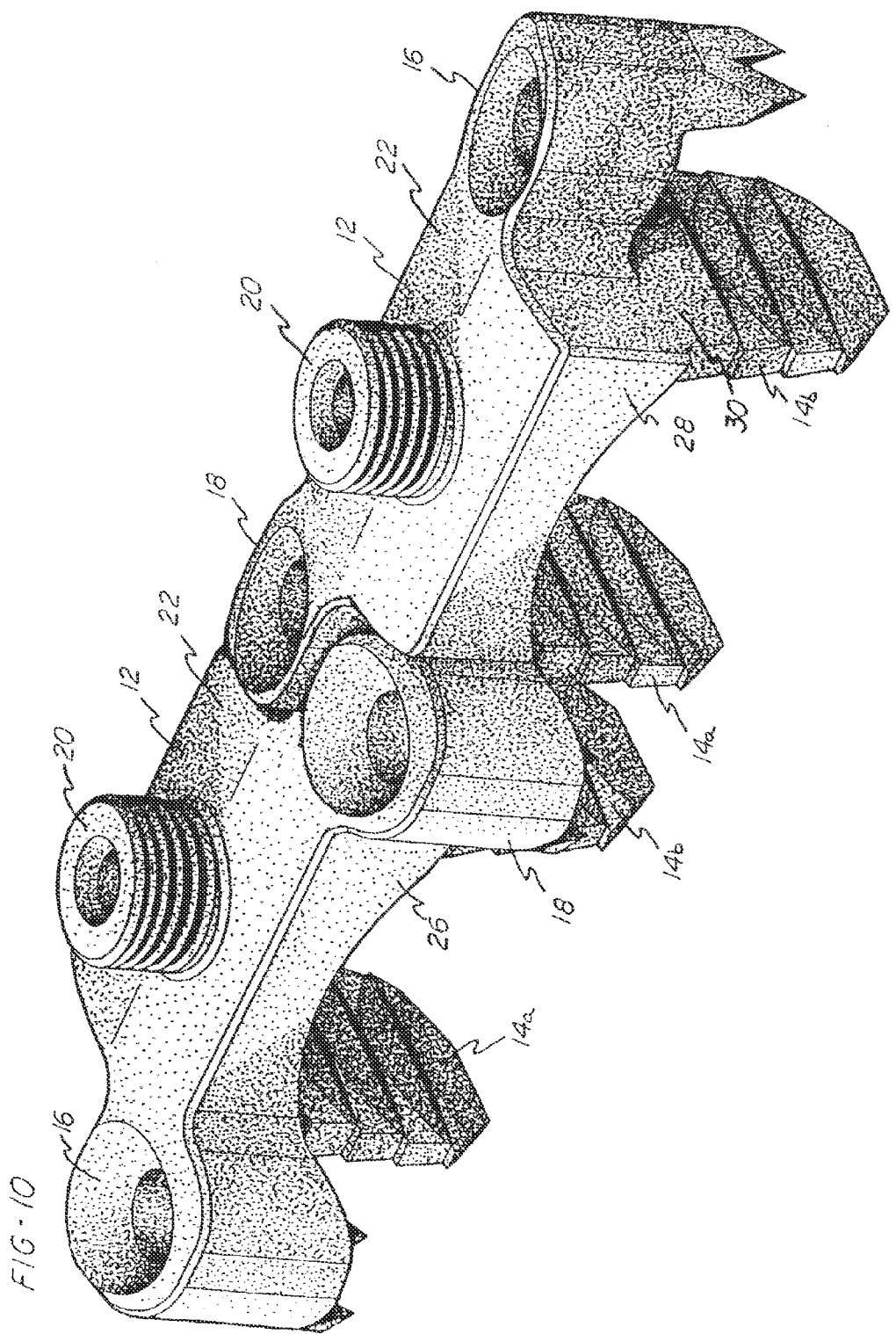
FIG. 10 is a perspective view of two of the alternative embodiment spinal staples aligned in end-to-end adjoining relationship.
Figure 11:
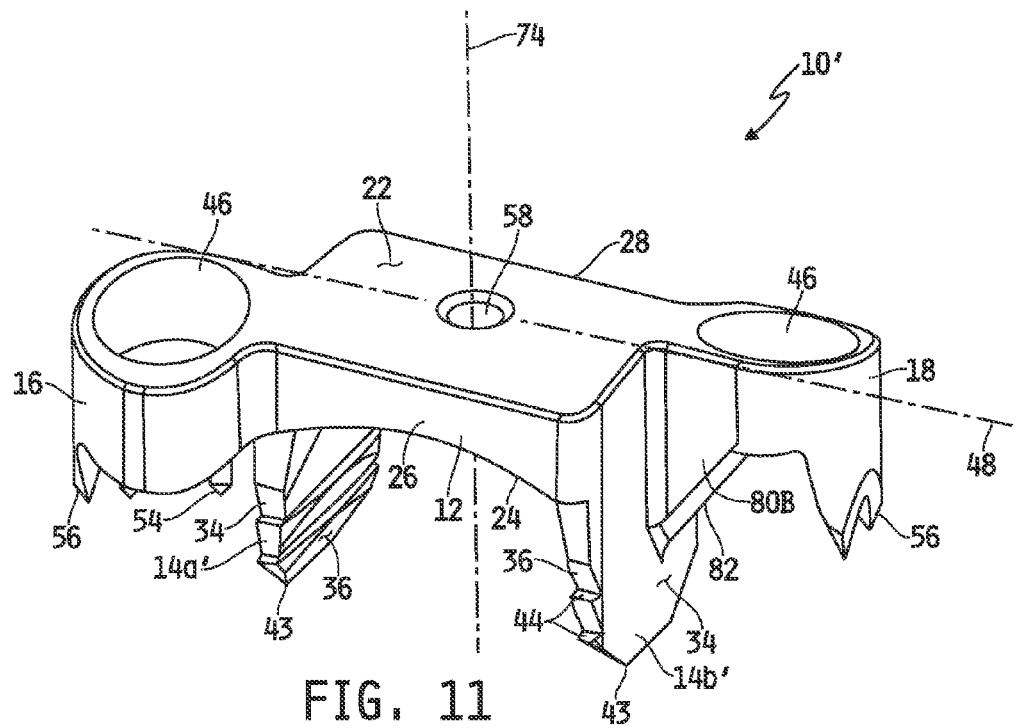
FIG. 11 is a top perspective view of a further illustrative embodiment spinal staple.
Figure 12:
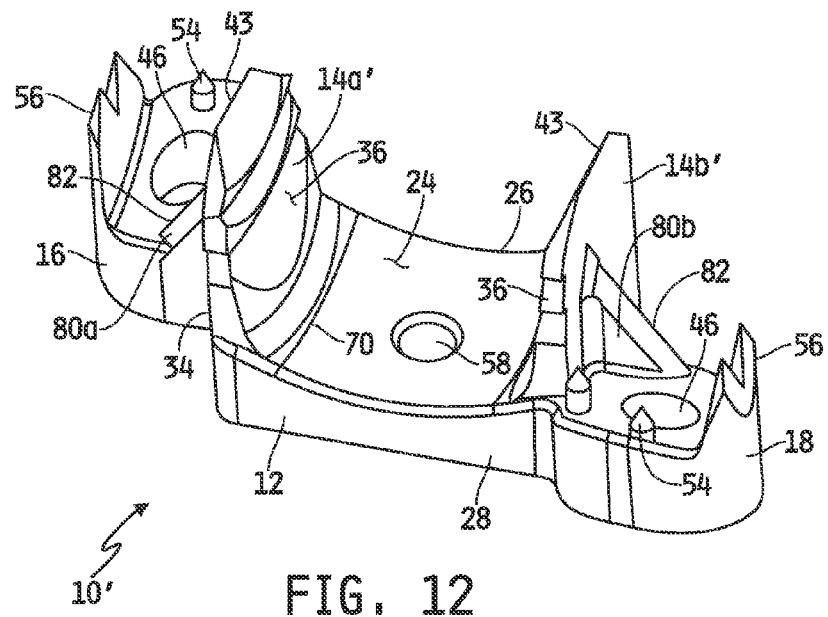
FIG. 12 is a bottom perspective view of the spinal staple of FIG. 11.
Figure 13:
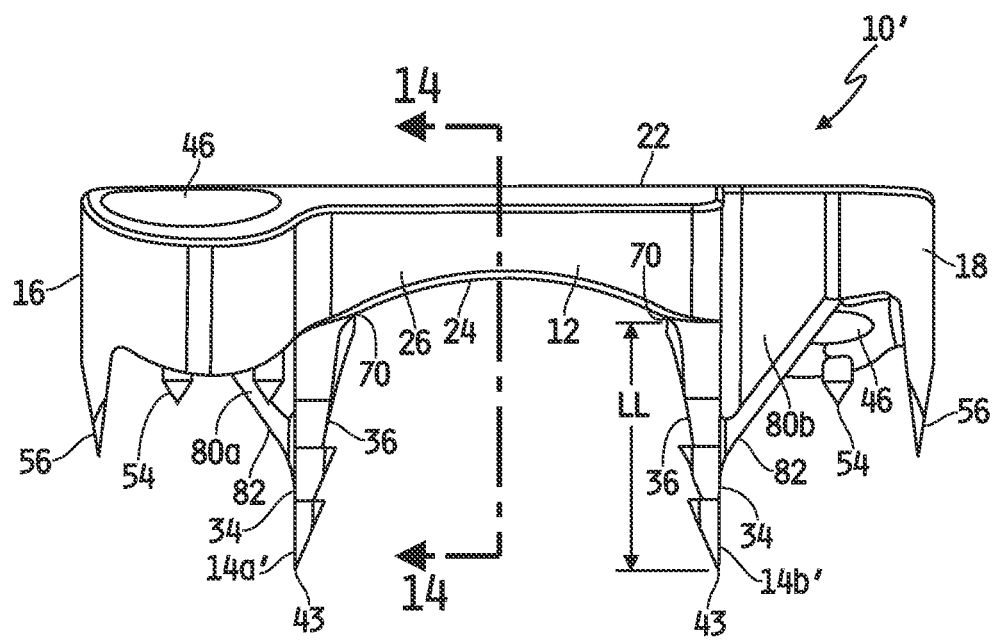
FIG. 13 is a side elevation view of the spinal staple of FIG. 11.

In an alternative embodiment, shown in FIGS. 9 and 10, the fastener retaining portions 16 and 18 may extend from opposite ends of the bridge member 12 such that both portions 16 and 18 lie to the same side of the longitudinal axis 48. In such an alternative embodiment, the staples 10 may be arranged in end-to-end abutting relation by rotating adjoining staples end-for-end 180°. Then, the left (right) fastener retaining portion 16 (18) of one staple 10 will lie alongside the left (right) fastener retaining portion 16 (18) of the adjoining staple 10. Moreover, the back side 51 of one fastener retaining portion 16, 18 will be in proximity to and facing the back side 51 of a second fastener retaining portion 16, 18.

Each of the fastener retaining portions 16 and 18 includes a recess, illustratively a counter sunk portion 50, adapted to receive the head of a fastener 68 therein. In addition, each fastener retaining portion 16, 18 also includes a lower surface 52 having a plurality of first pointed projections 54 extending downwardly therefrom for engaging underlying bone. Second pointed projections, or barbs 56, also extend downwardly from the fastener retaining portions 16, 18.

As shown in FIG. 2, the pointed barbs 56 have a length greater than the pointed projections 54 and are positioned at outer extremities of the retaining portions 16 and 18 to resist rotational movement of the staple 10 about its center axis.

The threaded post 20 extends upwardly from the upper surface 22 of the bridge member 12. The threaded post 20 cooperates with the bridge member 12 to define a passageway 58 coaxial with the post 20 and extending through the post 20 to the lower surface 24 of the bridge member 12. The threaded post 20 permits the attachment of additional hardware or instruments to the staple 10, while the passageway 58 allows for the passage of a guide wire for movement therealong, if desired. Further, the cannulated threaded post 20 facilitates attachment of a threaded removable, cannulated impaction device.

The staple 10 may be made of titanium, surgical stainless steel, or any other material which is sufficiently strong to resist the growth of a spinal column, maintains sufficient mechanical fatigue properties, and is sufficiently non-reactive in the environment of a living animal.

Figure 7:
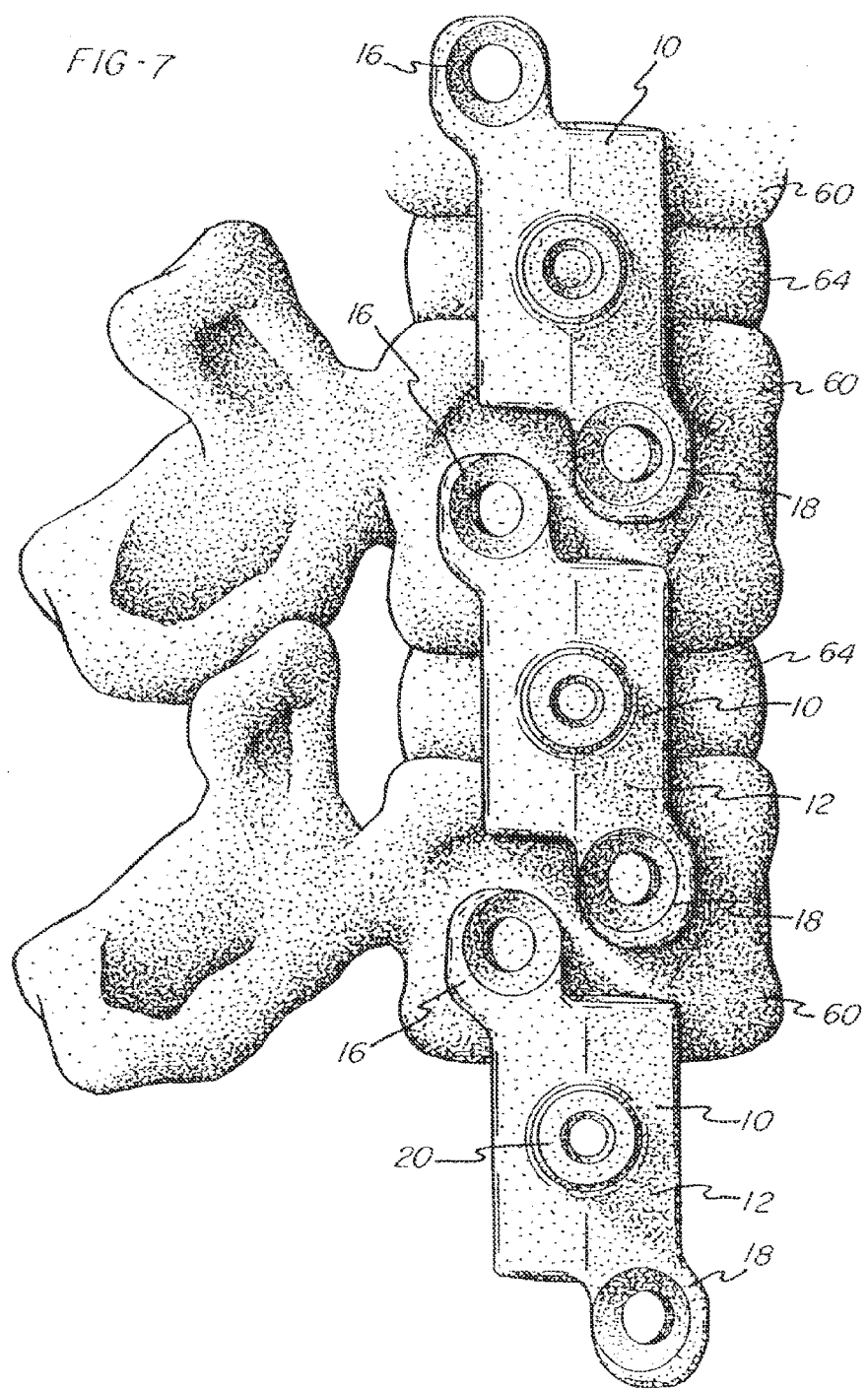
FIG. 7 is a top plan view of three of the spinal staples of the invention installed in a spine in end-to-end relationship.

Referring to FIGS. 7 and 8, the staples 10 are inserted into the vertebrae 60 of an animal having an immature or growing spine exhibiting scoliosis or other spinal deformity. The staples 10 are of a size such that the legs 14 are spaced far enough apart that the staples 10 will bridge longitudinally or lengthwise aligned, adjoining vertebrae 60 having confronting endplate growth centers 62 with predetermined thicknesses, and an intervening disk 64 therebetween. The staples 10 are driven into an intermediate portion 66, between endplate growth centers 62, of adjoining vertebrae 60 on the convex side of the curved spine. The legs 14 are of such a length that they extend into the vertebrae 60 no more than one-half the transverse diameter of each vertebra 60 to ensure that pressure is applied to only one side of the vertebrae 60. When positioned properly, the legs 14 are fully embedded in the vertebrae 60, and the projections 54 and barbs 56 of the fastener retaining portions 16, 18 engage the vertebral surfaces. Once a staple 10 is in place, fasteners 68 such as screws including threaded portions, barbed stakes, or the like are inserted through the passageways 46 in the fastener retaining portions 16, 18 and into the vertebrae 60.

The spinal correction system, when installed on a growing spine having abnormal curvature defining a convex side and an opposed concave side, with the spine including a plurality of lengthwise adjoining vertebrae 60 each having a pair of endplate growth centers 62, or longitudinal growth plates, with an intermediate portion 66 in between, the vertebrae 60 also having a particular transverse diameter, width, or thickness in a direction measured from the convex side to the concave side, is broadly seen to include a first bone engaging means or leg 14 that penetrates the convex side of an intermediate portion 66 of a first vertebra 60a to a depth of less than one-half the diameter of the first vertebra 60a, a second bone engaging means or leg 14 penetrating the convex side of an intermediate portion 66 of a second vertebra 60b to a depth of less than one-half the diameter of the second vertebra 60b, and a bridge member 12 connecting, illustratively rigidly, the first and second bone engaging means 14 (FIG. 8). As may be appreciated, the concave lower surface 24 of each staple 10 substantially matches or follows the contour of the vertebral body defined by the vertebrae 60.

The spinal correction system 10 thus corrects the abnormal curvature of the growing spine by inhibiting or retarding the growth of the endplate growth centers 62 captured between the first and second bone engaging means 14 on the convex side of the spine, while permitting the unrestrained growth of the endplate growth centers 62 on the concave side of the spine. As the spine continues to grow, the concave side of the spine will grow faster relative to the convex side, thereby resulting in slowing curve progression, and possibly in flattening of the curvature and straightening of the spine.

While the legs 14 are primarily responsible for restraining the growth of the endplate growth centers 62 captured therebetween, it will be seen that the fastener retaining portions 16, 18 and fasteners 68 also contribute to restraining the growth of the endplate growth centers 62 captured therebetween. The legs 14 may even be omitted provided that the fastener retaining portions 16, 18 and cooperating fasteners 68 are adapted to sufficiently resist the spreading forces due to lengthwise growth of the endplate growth centers 62.

A further illustrative embodiment spinal staple 10' is shown in FIGS. 11-14. The spinal staple 10' includes many of the same features of the earlier described spinal staple 10. As such, in the following description, like reference numbers identify like components as detailed with respect to the embodiment of FIGS. 1-10.

The inner surfaces 36 of the left and right legs 14a' and 14b' are configured to distribute compression pressure on the endplate growth centers 62 of vertebrae 60 in a manner slowing growth unilaterally and avoiding bone plowing. The spinal staple 10' is configured to induce a particular pattern of compression distribution. Factors that affect the distribution pattern of the compression within the endplate growth centers 62 include the length and width of the legs 14', which together define the transverse cross-sectional area of the legs 14', along with other structural features of the staple 10 and the placement of the legs 14' within the vertebrae 60. Bone plowing tends to relieve the therapeutic pressure place on the endplate grow centers 62 of the vertebrae 60, thereby allowing the disease to progress.

Sufficient transverse cross-sectional area of legs 14' ensures adequate contact surface against the vertebrae 60 to compress sufficient endplate growth centers 62, to provide an appropriate pattern of compression distribution, to prevent plowing, and to reduce joint motion. As shown in the illustrative embodiment of FIG. 15, the transverse cross-sectional area (LA) of the legs 14a' and 14b' is at least 10 percent of the cross-sectional area (VA) of the first vertebra 60a and the second vertebra 60b, respectively. In one illustrative embodiment, the cross-sectional area (LA) of the legs 14a' and 14b' is between 10 percent and 25 percent of the vertebral cross-sectional area (VA).

Figure 14:
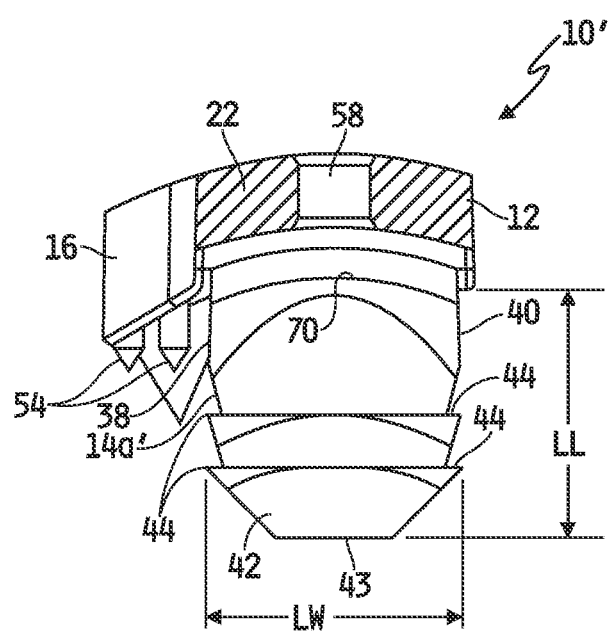
FIG. 14 is a transverse cross-sectional view taken along line 14-14 of FIG. 13.

In the illustrative embodiment of FIG. 14, the width (LW) of each leg 14', as measured generally from the front surface 38 to the back surface 40, is greater than about 6 millimeters (0.236 inches). In one illustrative embodiment, the width (LW) is between 7 millimeters (0.276 inches) and 14 millimeters (0.552 inches).

Figure 15:
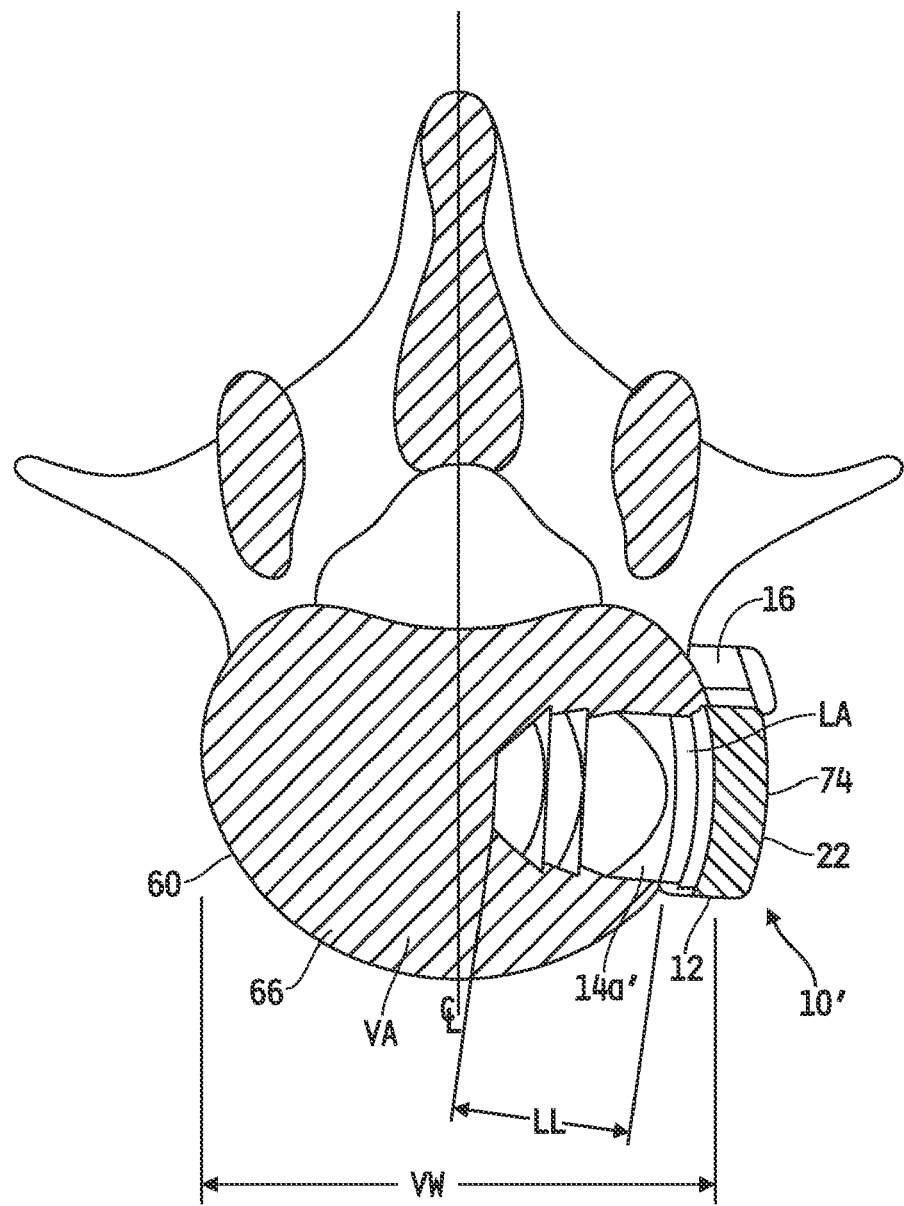
FIG. 15 is a transverse cross-sectional view showing the spinal staple of FIG. 11 installed in a vertebra.

Further, as detailed above, the length (LL) of each leg 14', as measured generally from the intersection 70 of the inner surface 36 and lower surface 24 to the tip edge 43, illustratively does not extend over one-half of the vertebral diameter or transverse width (VW) (FIG. 15). In one illustrative embodiment, the length (LL) of each leg 14a' and 14b' is between 10 percent and 40 percent of the transverse width (VW) of the first vertebra 60a and the second vertebra 60b, respectively. As such, based upon vertebral dimensions of skeletal immature children, the length (LL) of each leg 14a' and 14b' is less than 24 millimeters (0.945 inches). In one illustrative embodiment, the length (LL) is between 3 millimeters (0.118 inches) and 15 millimeters (0.59 inches).

The relationship of leg width (LW) to length (LL) may be adjusted to take into account the patient's size requirement or scale. In other words, in larger people a longer leg length (LL) may be justified. Likewise, the width (LW) should be wider to support a greater load related to the patient's greater dynamic loads, muscle forces, forces of motion, and vertebral/physeal cross-sectional area. The greater the cross-sectional area of the endplate growth center 62, the greater the forces generated by growth. Therefore, the ratio of leg width (LW) to leg length (LL) should be considered when taking into account the variation of the mass and size of the patient, and the cross-sectional area (VA) of the vertebrae 60 as a function of age and vertebral level in particular. For example, the upper thoracic spine is much smaller than that of the lower thoracic or lumbar spine, and the vertebral bodies of a young child are generally smaller than those of an adolescent. The ratio of staple leg length (LL) to the staple leg width (LW) is also important to generate the proper pattern of compressive stress gradient across the coronal plane of the vertebral endplate growth center 62, slowing or stopping growth on the stapled side of the vertebrae 60 and allowing unrestrained growth on the unstapled side of the vertebrae 60.

In the illustrative embodiment, the ratio of leg width (LW) to length (LL) is greater than about one-half. In other words, the width (LW) of the staple leg 14' is at least about 50 percent of its length (LL).

Referring further to FIGS. 11-13 and 16-18, an anti-rotation member 80 is located outboard of each staple leg 14' and abuts an adjacent fastener retaining portion 16,18. More particularly, a left anti-rotation member 80a extends between the left fastener retaining portion 16 and the left leg 14a, and a right anti-rotation member 80b extends between the right fastener retaining portion 18 and the right leg 14b. The anti-rotation members 80 are positioned outboard to the staple legs 14 to bite into the bone of vertebrae 60 without cutting into the endplate growth centers 62. The left and right anti-rotation members 80a and 80b are configured to reduce relative rotation of the left and right fastener retaining portions 16 and 18 about the longitudinal axis 48 relative to the first and second vertebrae 60a and 60b, respectively.

Each anti-rotation member 80 includes a lower edge 82 configured to engage the bone of the vertebra 60 such that it is anchored. More particularly, the lower edge 82 of the left anti-rotation member 80a is configured to engage the first vertebra 60a, and the lower edge 82 of the right anti-rotation member 80b is configured to engage the second vertebra 60b. As such, the lower edge 82 may be sharpened such that it cuts into the vertebral bone. The lower edge 82 illustratively extends parallel to the longitudinal axis 48 and upwardly from the leg 14' to the respective fastener retaining portion 16, 18. More particularly, each anti-rotation member 80 extends from proximate the center of the outer surface 34 of leg 14' to the fastener retaining portion 16, 18. In the illustrative embodiment, the anti-rotation members 80 comprise triangular shaped plates that appear as gussets. However, it should be appreciated that the anti-rotation members 80 could be formed of plates defining other shapes, such as rectangles or semi-circles.

The anchoring of the anti-rotation members 80 within the bone increases the load required to dislodge the staple 10' from relative rotation of the first and second vertebrae 60a and 60b bridged by the staple 10'. Moreover, the anti-rotation members 80 may assist in preventing the bending of the legs 14' relative to the bridge member 12, and the formation of rotational deformity. The anti-rotation members 80 may also help prevent relative rotation between the first and second vertebrae 60a and 60b about the longitudinal axis of the spine and the flexion-extension axis. The anti-rotation members 80 also may reduce the likelihood of relative movement of the staple 10' to the vertebrae 60 to improve stability. More particularly, the anti-rotation members 80 may help prevent rotation of the staple 10' relative to the first and second vertebrae 60a and 60b about the longitudinal axis of the spine and the axis 74 extending through the opening 58 of the staple 10'.

Figure 16:
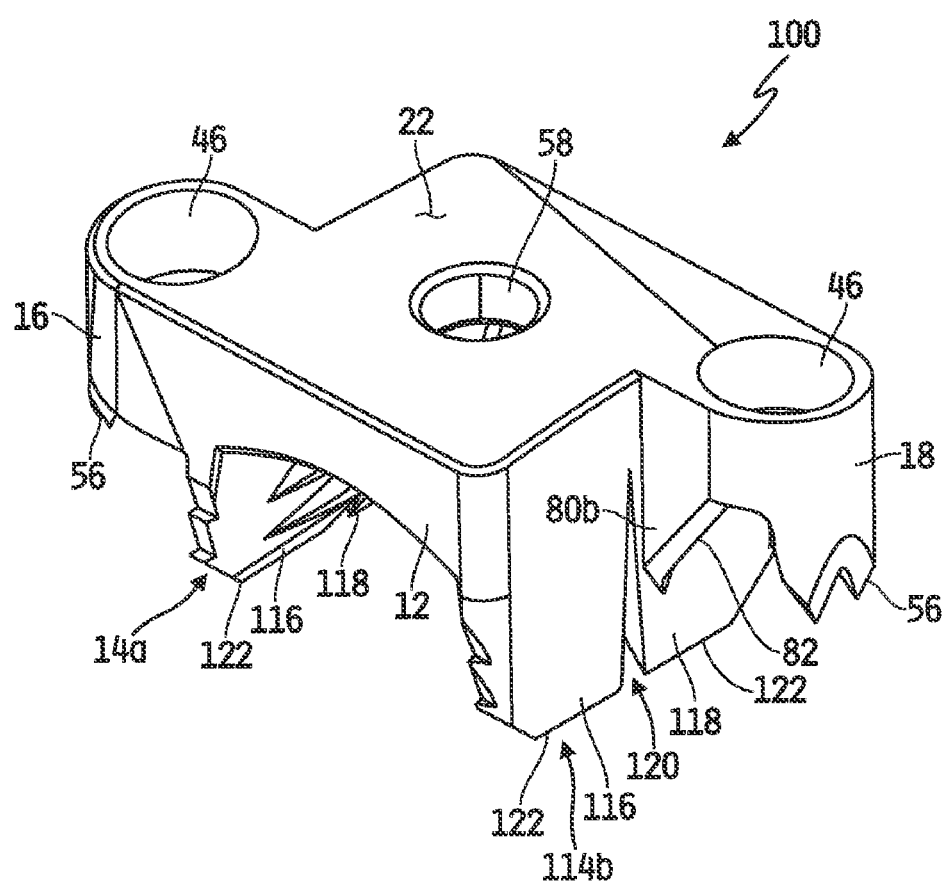
FIG. 16 is a perspective view of a further illustrative embodiment spinal staple.
Figure 17:
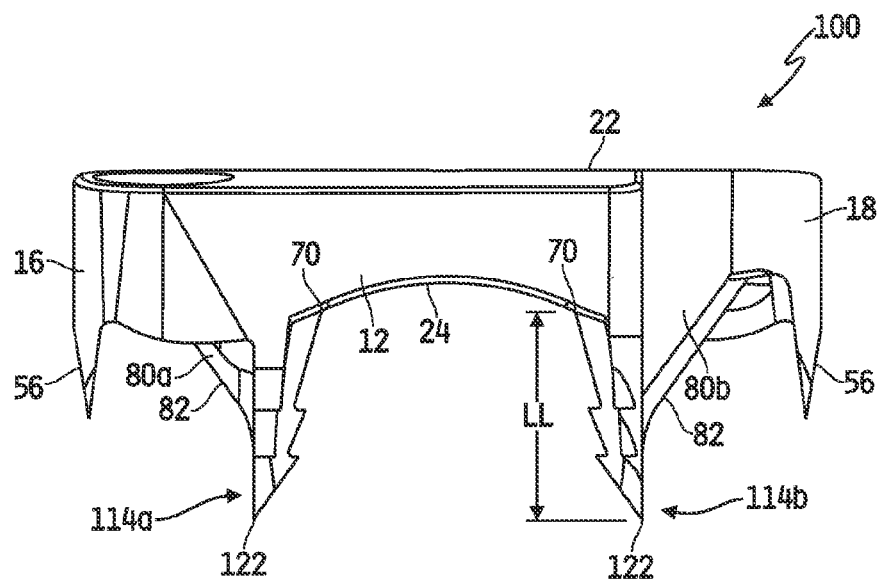
FIG. 17 is a side elevation view of the spinal staple of FIG. 16.
Figure 18:
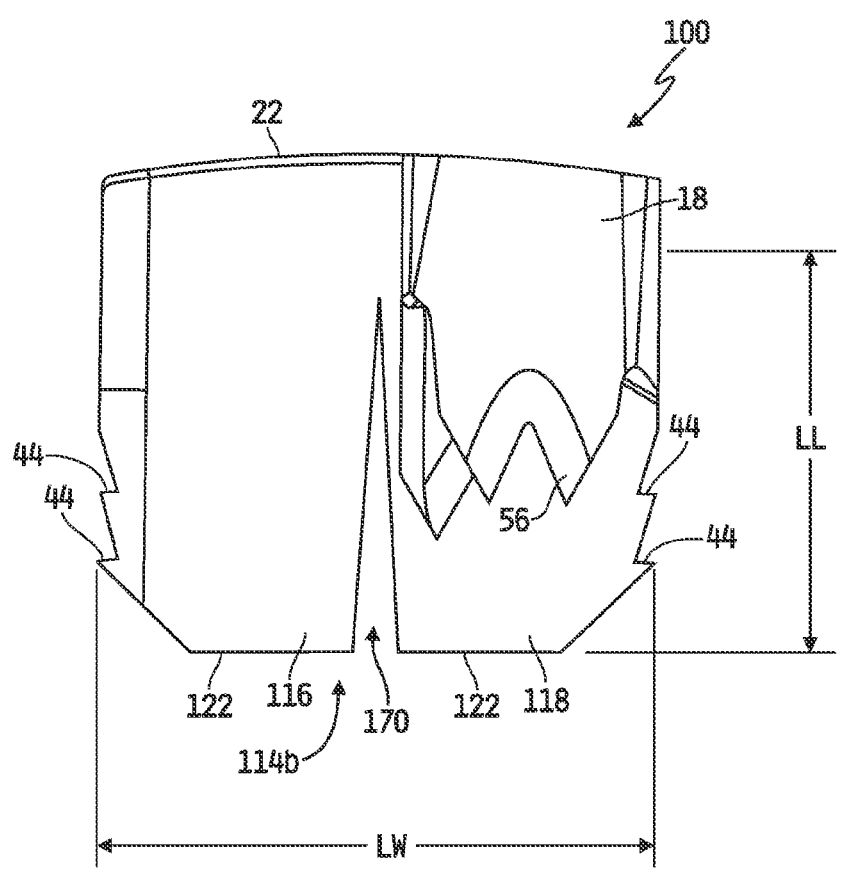
FIG. 18 is an end view of the spinal staple of FIG. 16.

Another illustrative embodiment spinal staple 100 is shown in FIGS. 16-18. The spinal staple 100 include many of the same features of the earlier described spinal staples 10, 10'. As such, in the following description, like reference numbers identify like components as detailed with respect to the embodiments of FIGS. 1-15.

The only significant distinction between the spinal staple 10' of FIGS. 11-15 and the spinal staple 100 of FIGS. 16-18, is that the legs 114a and 114b of the staple 100 include first and second portions 116 and 118 separated by a void or space 120. The reduced area of tip edges 122 of the portions 116 and 118 may result in easier insertion of the legs 114 into the bone of the vertebrae 60.

If the legs 114 are separated into individual portions 116 and 118, the collective dimensions thereof should illustratively satisfy the criteria detailed above with respect to the legs 14' of staple 10'. More particularly, in order to ensure adequate contact surface against the vertebrae 60, the collective transverse cross-sectional area (LA) of the portions 116 and 118 of each leg 114 is illustratively at least 10 percent, and in one illustrative embodiment not more than 25 percent, of the vertebral cross sectional area (VA) of the first vertebra 60a and the second vertebra 60b, respectively. Further, the collective width (LW) of each leg 114 is greater than about 6 millimeters (0.236 inches), and illustratively between 7 millimeters (0.276 inches) and 14 millimeters (0.552 inches). Also, the length (LL) of each portion 116 and 118 of legs 114 does not extend over one-half of the vertebral transverse width (VW), and is illustratively less than 24 millimeters (0.945 inches). Finally, the collective leg width (LW) of each leg 114 is illustratively at least about 50 percent of the average length (LL) of the portions 116 and 118.

While the above detailed embodiments illustrate a single staple 10, 10', 100 extending between first and second vertebra 60a and 60b, it should be appreciated that multiple, laterally spaced staples 10, 10', 100 may be utilized. In such a situation, the collective dimensions of the legs 14, 14', 114 within each vertebra 60a, 60b should illustratively satisfy the criteria detailed above with respect to the legs 14', 114 of staple 10', 100.

While the spinal correction system is intended primarily for correcting abnormal lateral curvature of an immature or growing spine, it may also be used for spinal correction in humans having mature or non-growing spines.

While the forms of apparatus herein described constitute preferred embodiments of this invention, it is to be understood that the invention is not limited to these precise forms of apparatus, and that changes may be made therein without departing from the scope of the invention which is defined in the appended claims.

What is claimed is:

1. A spinal staple comprising:
    a bridge member having an upper surface, an opposed lower surface, a front side, an opposed back side, a left end, and an opposed right end;
    a left leg extending from the lower surface of the bridge member proximate the left end to a tip defining a tapered bone penetrating blade edge configured to be inserted into a first vertebra, the left leg including an outer surface, an opposed inner surface, a front surface, and an opposed back surface;
    the left leg further including a width measured from the front surface to the back surface, and a length measured from the intersection of the inner surface of the left leg and the lower surface of the bridge member to the tip, the width of the left leg being at least one-half of the length of the left leg;
    a right leg extending from the lower surface of the bridge member proximate the right end to a tip defining a tapered bone penetrating blade edge configured to be inserted into a second vertebra, the right leg including an outer surface, an opposed inner surface, a front surface, and an opposed back surface;
    the right leg further including a width measured from the front surface to the back surface, and a length measured from the intersection of the inner surface of the right leg and the lower surface of the bridge member to the tip, the width of the right leg being at least one-half of the length of the right leg;
    a left fastener retaining portion extending from the bridge member left end and configured to support a left fastener for insertion into the first vertebra;
    wherein the left leg is positioned intermediate the bridge member and the left fastener retaining portion;
    a right fastener retaining portion extending from the bridge member right end and configured to support a right fastener for insertion into the second vertebra; and
    wherein the right leg is positioned intermediate the bridge member and the right fastener retaining portion.

2. The spinal staple of claim 1, wherein the width of the left leg is greater than about 6 millimeters, and the width of the right leg is greater than about 6 millimeters.

3. The spinal staple of claim 1, wherein the first and second vertebrae each include predetermined transverse widths, the length of the left leg is less than one-half the transverse width of the first vertebra, and the length of the right leg is less than one-half the transverse width of the second vertebra.

4. The spinal staple of claim 3, wherein the length of the left leg is no greater than 40 percent of the transverse width of the first vertebra, and the length of the right leg is no greater than 40 percent the transverse width of the second vertebra.

5. The spinal staple of claim 1, wherein:
    the first and second vertebrae each include transverse cross-sectional areas;
    the left leg includes a transverse cross-sectional area extending from the front surface to the back surface, the cross-sectional area being between 10 percent and 25 percent of the cross-sectional area of the first vertebra; and
    the right leg includes a transverse cross-sectional area extending from the front surface to the back surface, the cross-sectional area being between 10 percent and 25 percent of the cross-sectional area of the second vertebra.

6. The spinal staple of claim 1, further comprising:
    a left fastener extending within the left fastener retaining portion and configured to be inserted into the first vertebra; and
    a right fastener extending within the right fastener retaining portion and configured to be inserted into the second vertebra.

7. The spinal staple of claim 1, further comprising a passageway extending through the bridge member from the upper surface to the lower surface, the passageway configured to receive a guidewire for guiding movement of the bridge member along the guidewire.

8. The spinal staple of claim 1, wherein the inner surfaces of the left leg and the right leg are splayed outwardly away from each other as measured from a plane passing between the left leg and the right leg substantially perpendicular to the bridge member.

9. A spinal correction system configured for use on a growing spine having abnormal curvature defining a convex side, the spine including a plurality of lengthwise adjoining first and second vertebrae, each vertebra including endplate growth centers with an intermediate portion therebetween, a transverse width and a transverse cross-sectional area, the spinal correction system comprising:
    at least one bridge member including an upper surface, an opposed lower surface, a front side, an opposed back side, a left end, and an opposed right end;
    at least one left leg coupled to the at least one bridge member and including a tip defining a tapered bone penetrating blade edge configured to be inserted into a first vertebra, the at least one left leg including an outer surface, an opposed inner surface, a front surface, an opposed back surface, a collective width measured from the front surface to the back surface, a length measured from the intersection of the inner surface of the at least one left leg and the lower surface of the bridge member to the tip, and a collective transverse cross-sectional area extending from the front surface to the back surface;

a left retaining surface supported by the at least one left leg, the left retaining surface configured to inhibit withdrawal of the at least one left leg from the first vertebra;

the length of each at least one left leg being no greater than 40 percent of the transverse width of the first vertebra;

the collective transverse cross-sectional area of the inner surface of the at least one left leg being at least 10 percent of the cross-sectional area of the first vertebra;

at least one right leg coupled to the at least one bridge member and including a tip defining a tapered bone penetrating blade edge configured to be inserted into a second vertebra, the at least one right leg including an outer surface, an opposed inner surface, a front surface, an opposed back surface, a collective width measured from the front surface to the back surface, a length measured from the intersection of the inner surface of the at least one right leg and the lower surface bridge member to the tip, and a collective transverse cross-sectional area extending from the front surface to the back surface;

a right retaining surface supported by the at least one right leg, the right retaining surface configured to inhibit withdrawal of the at least one right leg from the second vertebra;

the length of each at least one right leg being no greater than 40 percent of the transverse width of the second vertebra;

the collective transverse cross-sectional area of the inner surface of the at least one right leg being at least 10 percent of the cross-sectional area of the second vertebra;

a left fastener retaining portion extending from each at least one bridge member left end;

a right fastener retaining portion extending from each at least one bridge member right end;

a left fastener extending within each left fastener retaining portion and configured to be inserted into the first vertebra; and a right fastener extending within each right fastener retaining portion and configured to be inserted into the second vertebra.

10. The spinal correction system of claim 9, wherein the at least one left leg includes a single left leg and the at least one right leg includes a single right leg.

11. The spinal correction system of claim 9, wherein the at least one left leg includes first and second left legs, and the at least one right leg includes first and second right legs.

12. The spinal correction system of claim 9, wherein:
the collective width of the at least one left leg is at least one-half of the average length of the at least one left leg; and
the collective width of the at least one right leg is at least one-half of the average length of the at least one right leg.

13. The spinal correction system of claim 9, wherein the inner surfaces of the at least one left leg and the at least one right leg are splayed outwardly as measured from a plane passing between the left leg and the right leg substantially perpendicular to the at least one bridge member.

14. A spinal correction system configured for use on a growing spine having abnormal curvature defining a convex side, the spine including a plurality of lengthwise adjoining vertebrae, each vertebra including endplate growth centers with an intermediate portion therebetween, a transverse width and a transverse cross-sectional area, the spinal correction system comprising:
at least one bridge member including an upper surface, an opposed lower surface, a front side, an opposed back side, a left end, and an opposed right end;
at least one left leg including a tip defining a tapered bone penetrating blade edge configured to be inserted into a first vertebra, the at least one left leg including an outer surface, an opposed inner surface, a front surface, and an opposed back surface,
the at least one left leg further including a collective width measured from the front surface to the back surface, and a length measured from the intersection of the inner surface of the at least one left leg and the lower surface of the bridge member to the tip,
the collective width of the at least one left leg being greater than one-half the average length of the at least one left leg;
at least one right leg including a tip defining a tapered bone penetrating blade edge configured to be inserted into a second vertebra, the at least one right leg including an outer surface, an opposed inner surface, a front surface, and an opposed back surface;
the at least one right leg further including a width measured from the front surface to the back surface, and a length measured from the intersection of the inner surface of the at least one right leg and the lower surface of the bridge member to the tip;
the collective width of the at least one right leg being greater than the one-half average length of the at least one right leg;
a left fastener retaining portion extending from the bridge member left end and configured to support a left fastener for insertion into the first vertebra;
wherein the left leg is positioned intermediate the bridge member and the left fastener retaining portion;
a right fastener retaining portion extending from the bridge member right end and configured to support a right fastener for insertion into the second vertebra; and
wherein the right leg is positioned intermediate the bridge member and the right fastener retaining portion.

15. The spinal correction system of claim 14, wherein the at least one left leg includes a single left leg and the at least one right leg includes a single right leg.

16. The spinal correction system of claim 14, wherein the at least one left leg includes first and second left legs, and the at least one right leg includes first and second right legs.

17. The spinal correction system of claim 14, wherein:
the at least one left leg includes a collective surface area of the inner surface extending from the front surface to the back surface of the at least one left leg;
the collective surface area of the inner surface of the at least one left leg is at least 10 percent of the cross-sectional area of the first vertebra;
the at least one right leg includes a collective surface area of the inner surface extending from the front surface to the back surface of the at least one right leg; and
the collective surface area of the inner surface of the at least one right leg is at least 10 percent of the cross-sectional area of the second vertebra.

18. The spinal correction system of claim 14, wherein:
the collective width of the at least one left leg is greater than about 6 millimeters; and
the collective width of the at least one right leg is greater than about 6 millimeters.

19. The spinal correction system of claim 14, wherein the length of each at least one left leg is no greater than 40 percent of the transverse width of the first vertebra, and the length of the right leg is no greater than 40 percent the transverse width of the second vertebra.

20. The spinal correction system of claim 14, wherein the inner surfaces of each at least one left leg and at least one right leg are splayed outwardly as measured from a plane passing between the at least one left leg and the at least one right leg substantially perpendicular to the bridge member.

21. A spinal correction system configured for use on a growing spine having abnormal curvature defining a convex side, the spine including a plurality of lengthwise adjoining vertebra, each vertebra including endplate growth centers with an intermediate portion therebetween, a transverse width and a transverse cross-sectional area, the spinal correction system comprising:
at least one bridge member including an upper surface, an opposed lower surface, a front side, an opposed back side, a left end, and an opposed right end;
at least one left leg extending from the lower surface of each at least one bridge member proximate the left end to a tip defining a tapered bone penetrating blade configured to be inserted into a first vertebra, the at least one left leg including an outer surface, an opposed inner surface, a front surface, and an opposed back surface, the at least one left leg further including a collective width measured from the front surface to the back surface, and a length measured from the intersection of the inner surface of the at least one left leg and the lower surface of the at least one bridge member to the tip;
the collective width of the at least one left leg being greater than about 6 millimeters and the length of each at least one left leg being less than about 24 millimeters;
at least one right leg extending from the lower surface of each at least one bridge member proximate the right end to a tip defining a tapered bone penetrating blade configured to be inserted into a second vertebra, the at least one right leg including an outer surface, an opposed inner surface, a front surface, and an opposed back surface, the at least one right leg further including a collective width measured from the front surface to the back surface, and a length measured from the intersection of the inner surface of the at least one right leg and the lower surface of the at least one bridge member to the tip;
the collective width of the at least one right leg being greater than about 6 millimeters and the length of each at least one right leg being less than about 24 millimeters;
a left fastener retaining portion extending from the left end of each of the at least one bridge member;
a right fastener retaining portion extending from the right end of each of the at least one bridge member;
a left fastener extending within the left fastener retaining portion and configured to be inserted into the first vertebra;
a right fastener extending within the right fastener retaining portion and configured to be inserted into the second vertebra;
wherein the left leg is positioned intermediate the bridge member and the left fastener retaining portion; and
wherein the right leg is positioned intermediate the bridge member and the right fastener retaining portion.

22. The spinal correction system of claim 21, wherein:
the collective width of the at least one left leg is between 7 millimeters and 14 millimeters and the length of each at least one left leg is between 3 millimeters and 15 millimeters; and
the collective width of the at least one right leg is between 7 millimeters and 14 millimeters and the length of each at least one right leg is between about 3 millimeters and 15 millimeters.

23. The spinal correction system of claim 21, wherein:
the collective width of the at least one left leg is at least one-half the average length of the at least one left leg; and
the collective width of the at least one right leg is at least one-half the average length of the at least one right leg.

24. The spinal correction system of claim 21, wherein the length of each at least one left leg is no greater than 40 percent of the transverse width of the first vertebra, and the length of each at least one right leg is no greater than 40 percent the transverse width of the second vertebra.

25. The spinal correction system of claim 21, wherein:
the at least one left leg includes a collective transverse cross-sectional area extending from the front surface to the back surface, the collective transverse cross-sectional area of the at least one left leg being between 10 percent and 25 percent of the cross-sectional area of the first vertebra; and
the at least one right leg includes a collective transverse cross-sectional area extending from the front surface to the back surface, the collective transverse cross-sectional area of the at least one right leg being between 10 percent and 25 percent of the cross-sectional area of the second vertebra.

26. The spinal correction system of claim 21, wherein the inner surfaces of each of the at least one left leg and right leg are splayed outwardly as measured from a plane passing between the at least one left leg and right leg substantially perpendicular to the at least one bridge member.

27. A spinal staple comprising:
a bridge member extending along a longitudinal axis and having an upper surface, an opposed lower surface, a front side, an opposed back side, a left end, and an opposed right end;
a left fastener retaining portion extending from the bridge member left end;
a left fastener extending within the left fastener retaining portion and configured to be inserted into a first vertebra;
a right fastener retaining portion extending from the bridge member right end;
a right fastener extending within the right fastener retaining portion and configured to be inserted into a second vertebra;
a left leg extending from the lower surface of the bridge member proximate the left end and including a tip configured to be inserted into the first vertebra, the left leg further including an outer surface, an opposed inner surface, a front surface, and an opposed back surface;
a right leg extending from the lower surface of the bridge member proximate the right end and including a tip configured to be inserted into the second vertebra, the right leg further including an outer surface, an opposed inner surface, a front surface, and an opposed back surface;
a left anti-rotation member extending between the left fastener retaining portion and the left leg, the left anti-rotation member configured to reduce relative rotation of the left fastener retaining portion about the longitudinal axis relative to the first vertebra; and a right anti-rotation member extending between the right fastener retaining portion and the right leg, the right anti-rotation member configured to reduce relative rotation of the right fastener retaining portion about the longitudinal axis relative to the second vertebra.

28. The spinal staple of claim 27, wherein the left anti-rotation member includes a lower edge configured to engage the first vertebra, and the right anti-rotation member includes a lower edge configured to engage the second vertebra.

29. The spinal staple of claim 28, wherein the lower edge of the left anti-rotation member extends upwardly from the left leg to the left fastener retaining portion, and the lower edge of the right anti-rotation member extends upwardly from the right leg to the right fastener retaining portion.

30. The spinal staple of claim 27, wherein the left anti-rotation member and the right anti-rotation member extend parallel to the longitudinal axis.

31. The spinal staple of claim 27, wherein the left anti-rotation member extends outwardly from proximate a center of the outer surface of the left leg, and the right anti-rotation member extends outwardly from proximate a center of the outer surface of the right leg.

32. The spinal staple of claim 27, wherein the anti-rotation members increase the load required to dislodge the staple from relative rotation of the first and second vertebrae bridged by the staple.

33. The spinal staple of claim 27, wherein:
the left leg includes a width measured from the front surface to the back surface, and a length measured from the intersection of the inner surface of the left leg and the lower surface of the bridge member to the tip, the width of the left leg being at least one-half of the length of the left leg; and
the right leg includes a width measured from the front surface to the back surface, and a length measured from the intersection of the inner surface of the right leg and the lower surface of the bridge member to the tip, the width of the right leg being at least one-half of the length of the right leg.

34. The spinal staple of claim 33, wherein the width of the left leg is greater than 6 millimeters, and the width of the right leg is greater than 6 millimeters.

35. A spinal correction system configured for use on a growing spine having abnormal curvature defining a convex side, the spine including a plurality of lengthwise adjoining first and second vertebrae, each vertebra including endplate growth centers with an intermediate portion therebetween, a transverse width and a transverse cross-sectional area, the spinal correction system comprising:

at least one bridge member including an upper surface, an opposed lower surface, a front side, an opposed back side, a left end, and an opposed right end;

at least one left leg coupled to the at least one bridge member and including a tip defining a tapered bone penetrating blade edge configured to be inserted into a first vertebra, the at least one left leg including an outer surface, an opposed inner surface, a front surface, an opposed back surface, a collective width measured from the front surface to the back surface, a length measured from the intersection of the inner surface of the at least one left leg and the lower surface of the bridge member to the tip, and a collective transverse cross-sectional area extending from the front surface to the back surface;

a left retaining surface supported by the at least one left leg, the left retaining surface configured to inhibit withdrawal of the at least one left leg from the first vertebra;

the length of each at least one left leg being no greater than 40 percent of the transverse width of the first vertebra;

the collective transverse cross-sectional area of the inner surface of the at least one left leg being at least 10 percent of the cross-sectional area of the first vertebra;

at least one right leg coupled to the at least one bridge member and including a tip defining a tapered bone penetrating blade edge configured to be inserted into a second vertebra, the at least one right leg including an outer surface, an opposed inner surface, a front surface, an opposed back surface, a collective width measured from the front surface to the back surface, a length measured from the intersection of the inner surface of the at least one right leg and the lower surface bridge member to the tip, and a collective transverse cross-sectional area extending from the front surface to the back surface;

a right retaining surface supported by the at least one right leg, the right retaining surface configured to inhibit withdrawal of the at least one right leg from the second vertebra;

the length of each at least one right leg being no greater than 40 percent of the transverse width of the second vertebra;

the left leg is positioned intermediate the bridge member and the left fastener retaining portion; and the right leg is positioned intermediate the bridge member and the right fastener retaining portion.

* * * * *

UNITED STATES PATENT AND TRADEMARK OFFICE
CERTIFICATE OF CORRECTION

| | | |
|---|---|---|
| PATENT NO. | : 8,021,403 B2 | Page 1 of 1 |
| APPLICATION NO. | : 11/126782 | |
| DATED | : September 20, 2011 | |
| INVENTOR(S) | : Eric J. Wall, Donita I. Bylski-Austrow and Joseph E. Reynolds | |

It is certified that error appears in the above-identified patent and that said Letters Patent is hereby corrected as shown below:

Title Page, Item (54) Title
The title should be --SPINAL CORRECTION SYSTEM--

Signed and Sealed this
Tenth Day of January, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,021,403 B2 | Page 1 of 1 |
| APPLICATION NO. | : 11/126782 | |
| DATED | : September 20, 2011 | |
| INVENTOR(S) | : Eric J. Wall, Donita I. Bylski-Austrow and Joseph E. Reynolds | |

It is certified that error appears in the above-identified patent and that said Letters Patent is hereby corrected as shown below:

Title Page, Item (54) and at Column 1, line 1
The title should be --SPINAL CORRECTION SYSTEM--

This certificate supersedes the Certificate of Correction issued January 10, 2012.

Signed and Sealed this
Fourteenth Day of February, 2012

David J. Kappos
*Director of the United States Patent and Trademark Office*